United States Patent
Walter et al.

(10) Patent No.: US 10,417,923 B2
(45) Date of Patent: Sep. 17, 2019

(54) SYSTEMS, APPARATUSES, AND METHODS FOR MEMORY RECALL AND REACTIVATION BY TARGETED STIMULATION

(71) Applicant: Lotus Magnus, LLC, Grove City, OH (US)

(72) Inventors: Timothy J. Walter, Upper Arlington, OH (US); Uma Marar, Blacklick, OH (US)

(73) Assignee: Lotus Magnus, LLC, Grove City, OH (US)

( * ) Notice: Subject to any disclaimer, the term of this patent is extended or adjusted under 35 U.S.C. 154(b) by 774 days.

(21) Appl. No.: 14/985,956

(22) Filed: Dec. 31, 2015

(65) Prior Publication Data
US 2017/0193831 A1 Jul. 6, 2017

(51) Int. Cl.
*G09B 5/02* (2006.01)
*A61B 5/00* (2006.01)
(Continued)

(52) U.S. Cl.
CPC ............. *G09B 5/02* (2013.01); *A61B 3/113* (2013.01); *A61B 5/01* (2013.01); *A61B 5/02405* (2013.01); *A61B 5/02438* (2013.01); *A61B 5/0476* (2013.01); *A61B 5/0478* (2013.01); *A61B 5/0488* (2013.01); *A61B 5/0496* (2013.01); *A61B 5/04842* (2013.01); *A61B 5/0816* (2013.01); *A61B 5/11* (2013.01); *A61B 5/486* (2013.01); *A61B 5/4809* (2013.01); *A61B 5/4812* (2013.01); *A61M 21/00* (2013.01); *A61M 21/02* (2013.01); *A61N 2/006* (2013.01); *G09B 5/06* (2013.01); *A61B 5/4806* (2013.01); *A61B 2018/00571* (2013.01); *A61M 2021/0016* (2013.01); *A61M 2021/0022* (2013.01); *A61M 2021/0027* (2013.01);
(Continued)

(58) Field of Classification Search
CPC ............. G09B 19/00; G09B 5/02; G09B 5/06
See application file for complete search history.

(56) References Cited

U.S. PATENT DOCUMENTS 3,160,159 A 12/1964 Borisovich et al.
3,388,699 A 6/1968 Webb et al.
(Continued)

OTHER PUBLICATIONS

"Battery-free, Wireless Encephalogram", MedGadget, Apr. 14, 2008, Online available at <http://www.medgadget.com/archives/2008/04/batteryfree_wireless_encephalogram>, Retrieved on Apr. 17, 2008, 6 pages.
(Continued)

*Primary Examiner* — Nathan Hillery
(74) *Attorney, Agent, or Firm* — Fiala & Weaver, P.L.L.C.

(57) ABSTRACT

Systems, apparatuses, and methods for memory recall and reactivation by targeted stimulation are provided. Systems, apparatuses, and methods are described for providing patterns of a reinforcing cue re-presentation during sleep. Systems, apparatuses, and methods are also described for determining patterns of a reinforcing cue for re-presentation during sleep. Systems, apparatuses, and methods are also described for determining reinforcing cues for re-presentation during sleep. Systems, apparatuses, and methods are also described for determining and predicting sleep intervals based only on sleep onset.

22 Claims, 10 Drawing Sheets

(51) Int. Cl.

| | |
|---|---|
| *A61M 21/02* | (2006.01) |
| *A61B 5/0478* | (2006.01) |
| *A61B 5/0484* | (2006.01) |
| *A61B 5/0488* | (2006.01) |
| *A61B 5/0496* | (2006.01) |
| *A61M 21/00* | (2006.01) |
| *A61N 2/00* | (2006.01) |
| *A61B 3/113* | (2006.01) |
| *A61B 5/01* | (2006.01) |
| *A61B 5/024* | (2006.01) |
| *A61B 5/0476* | (2006.01) |
| *A61B 5/08* | (2006.01) |
| *A61B 5/11* | (2006.01) |
| *G09B 5/06* | (2006.01) |
| *G09B 19/00* | (2006.01) |
| *A61B 18/00* | (2006.01) |
| *A61N 5/06* | (2006.01) |

(52) U.S. Cl.
CPC .............. *A61M 2021/0044* (2013.01); *A61M 2205/502* (2013.01); *A61M 2230/10* (2013.01); *A61M 2230/18* (2013.01); *A61M 2230/60* (2013.01); *A61N 2005/0653* (2013.01); *G09B 19/00* (2013.01)

(56) References Cited

U.S. PATENT DOCUMENTS

| | | | |
|---|---|---|---|
| 3,495,596 | A | 2/1970 | Condict |
| 5,356,368 | A | 10/1994 | Monroe et al. |
| 5,551,879 | A | 9/1996 | Raynie et al. |
| 5,601,090 | A | 2/1997 | Musha |
| 5,769,778 | A | 6/1998 | Abrams et al. |
| 5,813,993 | A | 9/1998 | Kaplan et al. |
| 5,954,667 | A | 9/1999 | Finkenzeller et al. |
| 5,999,846 | A | 12/1999 | Pardey et al. |
| 6,052,619 | A | 4/2000 | John |
| 6,161,030 | A | 12/2000 | Levendowski et al. |
| 6,167,298 | A | 12/2000 | Levin |
| 6,230,049 | B1 | 5/2001 | Fischell et al. |
| 6,272,378 | B1 | 8/2001 | Baumgart-Schmitt |
| 6,381,481 | B1 | 4/2002 | Levendowski et al. |
| 6,385,486 | B1 | 5/2002 | John et al. |
| 6,425,852 | B1 | 7/2002 | Epstein et al. |
| 6,496,724 | B1 | 12/2002 | Levendowski et al. |
| 6,497,658 | B2 | 12/2002 | Roizen et al. |
| 6,625,485 | B2 | 9/2003 | Levendowski et al. |
| 6,640,122 | B2 | 10/2003 | Manoli et al. |
| 6,926,660 | B2 | 8/2005 | Miller et al. |
| 6,950,697 | B2 | 9/2005 | Jordan et al. |
| 6,978,179 | B1 | 12/2005 | Flagg et al. |
| 6,984,202 | B2 | 1/2006 | Ashenden et al. |
| 7,024,234 | B2 | 4/2006 | Margulies et al. |
| 7,104,947 | B2 | 9/2006 | Riehl |
| 7,153,256 | B2 | 12/2006 | Riehl et al. |
| 7,223,245 | B2 | 5/2007 | Zoth et al. |
| 7,297,119 | B2 | 11/2007 | Westbrook et al. |
| 8,382,484 | B2 | 2/2013 | Wetmore et al. |
| 9,149,599 | B2 | 10/2015 | Walter et al. |
| 2003/0131351 | A1* | 7/2003 | Shapira .................... A61B 5/16 725/24 |
| 2003/0144603 | A1* | 7/2003 | Zoth ...................... A61B 5/121 600/559 |
| 2003/0149344 | A1* | 8/2003 | Nizan ..................... A61B 5/486 600/300 |
| 2003/0199945 | A1 | 10/2003 | Ciulla et al. |
| 2004/0153129 | A1* | 8/2004 | Pless ................... A61B 5/0476 607/62 |
| 2004/0234103 | A1 | 11/2004 | Steffein et al. |
| 2005/0020934 | A1 | 1/2005 | Potter et al. |
| 2005/0165323 | A1 | 7/2005 | Montgomery et al. |
| 2005/0177058 | A1* | 8/2005 | Sobell ................. A61B 5/0484 600/545 |
| 2005/0182287 | A1 | 8/2005 | Becker et al. |
| 2005/0234518 | A1 | 10/2005 | Heruth et al. |
| 2005/0256539 | A1 | 11/2005 | George et al. |
| 2005/0268916 | A1 | 12/2005 | Mumford et al. |
| 2005/0277821 | A1 | 12/2005 | Payne, Jr. |
| 2006/0094971 | A1 | 5/2006 | Drew |
| 2006/0106275 | A1 | 5/2006 | Raniere et al. |
| 2006/0205993 | A1 | 9/2006 | Fischell et al. |
| 2007/0027388 | A1 | 2/2007 | Chou |
| 2007/0287896 | A1 | 12/2007 | Derchak et al. |
| 2008/0071150 | A1 | 3/2008 | Miesel et al. |
| 2008/0081941 | A1 | 4/2008 | Tononi |
| 2008/0146893 | A1 | 6/2008 | Levendowski et al. |
| 2008/0214903 | A1* | 9/2008 | Orbach .................. A61B 5/486 600/301 |
| 2008/0218311 | A1 | 9/2008 | Pless et al. |
| 2009/0149721 | A1* | 6/2009 | Yang .................... A61B 5/0002 600/301 |
| 2010/0163027 | A1* | 7/2010 | Hyde ..................... G06F 19/00 128/203.12 |
| 2010/0168525 | A1* | 7/2010 | Hyde ..................... G06F 19/00 600/300 |
| 2010/0168602 | A1* | 7/2010 | Hyde .................. A61B 5/0484 600/544 |
| 2010/0234697 | A1 | 9/2010 | Pless |
| 2010/0240945 | A1* | 9/2010 | Bikko ................ A61B 5/02405 600/28 |
| 2011/0183305 | A1* | 7/2011 | Orbach ................... A61B 5/16 434/236 |
| 2012/0251989 | A1 | 10/2012 | Wetmore et al. |
| 2013/0190556 | A1 | 7/2013 | Wetmore et al. |
| 2014/0057232 | A1 | 2/2014 | Wetmore et al. |
| 2014/0347265 | A1* | 11/2014 | Aimone ................. G09G 3/003 345/156 |
| 2014/0370479 | A1* | 12/2014 | Gazzaley ............... A61B 5/162 434/322 |
| 2015/0379878 | A1 | 12/2015 | Walter et al. |

OTHER PUBLICATIONS

"Pilot Test of Fatigue Management Technologies", Federal Motor Carrier Safety Administration, Feb. 2005, Online available at <http://www.fmcsa.dot.gov/facts-research/research-technology/tech/PilotTest-of-FatigueManagementTechnologies-031005.htm>, Retrieved on Mar. 28, 2008, 4 pages.

"Wireless BEG Powered by Body Heat", MedGadget, Oct. 31, 2007, Online available at <URL:http://www.medgadget.com/archives/2007/10/wireless_eeg_powered_by_body_heat.htm>, Retrieved on Apr. 17, 2008, 6 pages.

Antony et al., "Cued Memory Reactivation During Sleep Influences Skill Learning", Nature Neuroscience, Advanced Online Publication, 2012, pp. 1-3.

Badillo et al., "EEG Digital System for Long Time Recording", Congreso Nacional De Instrumentacion, Memorias Somi XV SIS-0, Oct. 25, 2002, 6 pages.

Bielikova, Maria, "A Body-Monitoring System with BEG and BOG Sensors", ERCIM News No. 51, Oct. 2002, Online available at <http://www.ercim.org/publication/Ercim_News/enw51/bielikova.htm>, 2 pages.

Born et al., "System Consolidation of Memory During Sleep", Psychological Research, 2012, vol. 76, Issue 2, pp. 192-203.

Smith et al., "Post Training REMs Coincident Auditory Stimulation Enhances Memory in Humans", Psychiatric Journal of the University of Ottawa, Jun. 1990, vol. 15, Issue 2, pp. 85-90.

Cavuoto, James (Ed.), "Alertness Monitoring Devices Emerge from San Diego", Neurotech Business Report, Oct. 2001, Online available at <http://www.neurotechreports.com/pages/alertness.html>, Retrieved on May 1, 2009, 2 pages.

Church et al., "Evoked K-Complexes and Cardiovascular Responses to Spindle-Synchronous and Spindle-Asychoronous Stimulus Clicks During NREM Sleep", Electroencephalography and Clinical Neurophysiology, 1978, vol. 45, pp. 443-453.

Huber et al., "TMS-Induced Cortical Potentiation during Wakefulness Locally Increases Slow Wave Activity during Sleep", PloS One, Mar. 2007, vol. 3 (e276), pp. 1-7.

(56) References Cited

OTHER PUBLICATIONS

Marshall et al., "Transcranial Direct Current Stimulation during Sleep Improves Declarative Memory", Journal of Neuroscience, Nov. 3, 2004, vol. 24, Issue 44, pp. 9985-9992.
Massimini et al., "Triggering Sleep Slow Waves by Transcranial Magnetic Stimulation", PNAS, May 15, 2007, vol. 104, Issue 2, pp. 8496-8501.
Prime et al., "Transcranial Magnetic Stimulation over Posterior Parietal Cortex Disrupts Transsaccadic Memory of Multiple Objects", Journal of Neuroscience, Jul. 2, 2008, vol. 28, Issue 27, pp. 6938-6949.
Schmidt et al., "Mobile Sleep Diagnostic Devices for Testing around the World", presented at Pan America Health Care Exchange (PAHCE) Longbeach-Los Angeles, CA, Feb. 12-16, 2007, 6 pages.
Tenenbaum, D., "Study puts us one step closer to understanding the function of sleep", Apr. 30, 2007, Online available at <URL:http://www.news.wisc.edu/13733>, Retrieved on Apr. 17, 2008, 3 pages.
Rasch et al., "Maintaining Memories During Reactivation", Current Opinion in Neurobiology, 2007, 17, pp. 698-703.
Rasch et al., "Odor Cues During Slow-Wave Sleep Prompt Declarative Memory Consolidation", Science, vol. 315, Mar. 9, 2007, pp. 1426-1429.
Rudoy et al., "Strengthening Individual Memories by Reactivating Them During Sleep", Science, vol. 326, Nov. 20, 2009, pp. 1079.
International Preliminary Report on Patentability received for PCT Patent Application No. PCT/US2008/078940, dated Oct. 12, 2010, 6 pages.

\* cited by examiner

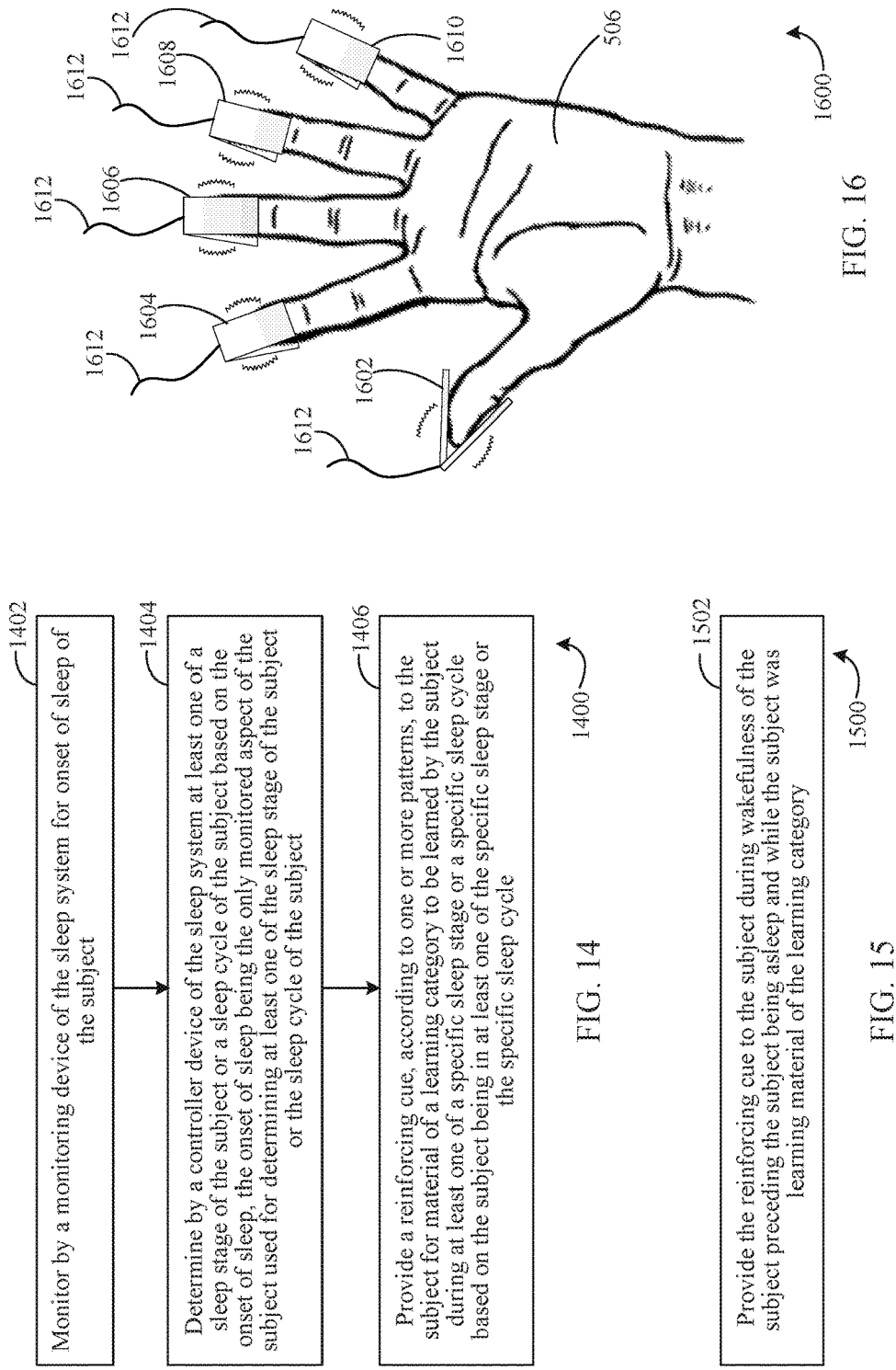

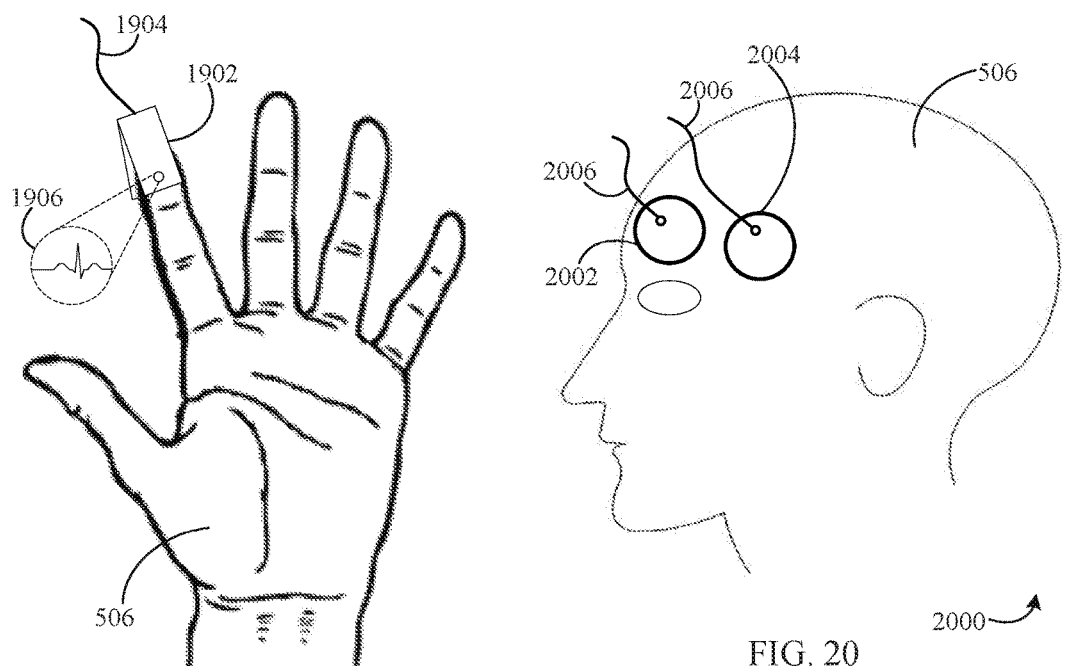

SYSTEMS, APPARATUSES, AND METHODS FOR MEMORY RECALL AND REACTIVATION BY TARGETED STIMULATION

CROSS-REFERENCE TO RELATED APPLICATIONS

This application is related to U.S. patent application Ser. No. 14/844,765, filed on Sep. 3, 2015, and entitled "BRAIN STIMULATION SYSTEMS AND METHODS," the entirety of which is incorporated by reference herein.

BACKGROUND

I. Technical Field

The present invention relates generally to systems, apparatuses, and methods for memory recall and reactivation by targeted stimulation.

II. Background

Sleep has been shown to be important in memory consolidation. Obtaining proper sleep prior to learning enhances the brain's ability to encode new information. Subjects who are allowed to sleep after learning perform better on subsequent recall than subjects who spend the same amount of time awake prior to retesting.

BRIEF SUMMARY

Methods, systems, and apparatuses are described for memory recall and reactivation by targeted stimulation, substantially as shown in and/or described herein in connection with at least one of the figures, as set forth more completely in the claims.

BRIEF DESCRIPTION OF THE DRAWINGS/FIGURES

The accompanying drawings, which are incorporated herein and form a part of the specification, illustrate embodiments and, together with the description, further serve to explain the principles of the embodiments and to enable a person skilled in the pertinent art to make and use the embodiments.

FIG. 14 is a flowchart for determining a sleep interval of a subject based on sleep onset, according to an exemplary embodiment.

FIG. 15 is a flowchart for memory encoding, according to an exemplary embodiment.

FIG. 16 is a diagram of a stimulation provision configuration for memory encoding, according to an exemplary embodiment.

FIG. 17 is a flowchart for providing primary reinforcing cues according to patterns, according to an exemplary embodiment.

FIG. 18 is a flowchart for testing post-sleep recall accuracy, according to an exemplary embodiment.

FIG. 19 is a diagram of a sensor configuration, according to an exemplary embodiment.

FIG. 20 is a diagram of a sensor configuration, according to an exemplary embodiment.

Embodiments will now be described with reference to the accompanying drawings. In the drawings, like reference numbers indicate identical or functionally similar elements. Additionally, the left-most digit(s) of a reference number identifies the drawing in which the reference number first appears.

DETAILED DESCRIPTION

I. Introduction

Figure 1:
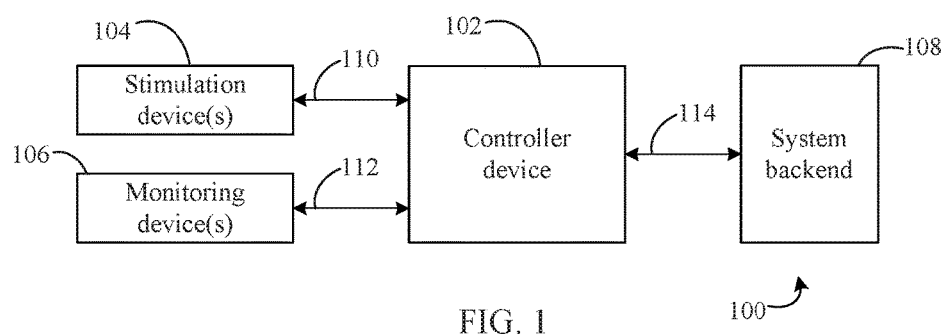
FIG. 1 is a block diagram of a system for memory recall and reactivation by targeted stimulation, according to an exemplary embodiment.

The present specification discloses numerous example embodiments. The scope of the present patent application is not limited to the disclosed embodiments, but also encompasses combinations of the disclosed embodiments, as well as modifications to the disclosed embodiments.

References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Furthermore, it should be understood that spatial descriptions (e.g., "above," "below," "up," "left," "right," "down," "top," "bottom," "vertical," "horizontal," etc.) used herein are for purposes of illustration only, and that practical implementations of the structures described herein can be spatially arranged in any orientation or manner.

Still further, it should be noted that the drawings/figures are not drawn to scale unless otherwise noted herein.

Additionally, in the discussions herein unless otherwise stated, adjectives such as "substantially," "approximately," and "about" modifying a condition or relationship characteristic of a feature or features of an embodiment of the disclosure, are understood to mean that the condition or characteristic is defined to be within tolerances that are acceptable for operation of the embodiment for an application for which it is intended.

Numerous exemplary embodiments are now described. Any section/subsection headings provided herein are not intended to be limiting. Embodiments are described throughout this document, and each embodiment may be eligible for inclusion within multiple different sections or subsections. Furthermore, it is contemplated that the disclosed embodiments may be combined with each other in any manner. That is, the embodiments described herein are not mutually exclusive of each other and may be practiced and/or implemented alone, or in any combination.

II. Example Embodiments

In embodiments, techniques for memory recall and reactivation by targeted stimulation are described. Embodiments described herein improve memory and learning abilities for subjects. For instance, the described techniques and embodiments include targeted stimulation for memory recall and reactivation in various learning categories, such as but not limited to, facts, creative thought, and motor skills, using reinforcing cues while a subject is asleep. Additionally, the described techniques and embodiments include variations in stimulation patterns to increase memory recall and reactivation efficacy. Sleep-related memory consolidation occurs normally but can also be enhanced through the disclosed techniques and embodiments.

The example techniques and embodiments described herein may be adapted to various types of systems, apparatuses, and devices, such as communication devices (e.g., cellular and smart phones, etc.), wearable electronic devices and/or sensors (e.g., the UP™ series of wearables from JAWBONE™, the Apple Watch from Apple, Inc., the series of fitness trackers from Fitbit, Inc., sensors from MC10, Inc., the Muse™ headband from InteraXon, Inc., the WatchPAT™ from Itamar Medical Ltd., etc.), motion sensors, bed pillow sensors, medical devices (e.g., heart monitors, electrical signal monitors, continuous positive airway pressure (CPAP) machines, etc.), computers/computing devices (laptops, tablets, desktops, etc.), computing systems, other electronic devices such as gaming consoles, other home electronics, and/or the like. While the embodiments herein may be described with respect to certain devices and systems as conceptual and/or illustrative examples for descriptive consistency, other types of device and system implementations are also contemplated by implementing the disclosed techniques. It is contemplated herein that in various embodiments and with respect to the illustrated figures of this disclosure, one or more components described and/or shown may not be included and that additional components may be included.

Electroencephalography (EEG) records the neural activity of electrical potential across cell membranes, which are detected through the cerebral cortex and recorded by a plurality of electrodes. The changes in electrical potential in the cortex contain rhythmical activity, which typically occur at frequencies of about 0.5 to 70 cycles per second (hertz). While awake, fast, random signals are predominantly generated at low voltage and mixed frequency. While asleep, more predictable signals are generated at a low voltage and predictable frequencies over predictable periods.

Five distinct brain wave patterns that are commonly detected during an EEG recording are delta waves (e.g., about 0.5-3 hertz), theta waves (e.g., about 3-8 hertz), alpha waves (e.g., about 8-12 hertz), beta waves (e.g., about 13-38 hertz), and gamma waves (e.g., about 38-70 hertz). Many of these frequencies may be observed in a subject's sleep cycle. A sleep cycle may be defined as a progression of brainwave patterns that may be seen while a subject is sleeping. Human adult sleep consists of four to five sleep cycles each night where each sleep cycle is about 90 minutes in length. Each sleep cycle contains various sleep stages such as Stage I, Stage II, Slow Wave Sleep, and Rapid Eye Movement (REM) Sleep. Each sleep stage consists of distinct brainwave patterns. In the context of this disclosure, sleep intervals refer to sleep stages, sleep cycles, progressions of sleep stages within a sleep cycle, and progressions of sleep cycles throughout a sleep period, as well as specific sleep activity having a having a perceivable duration.

During stage I sleep, a subject's brain waves slow in frequency transitioning from alpha waves to theta waves. During stage II sleep, a subject's brain waves slow further and include various bursts of activity such as sleep spindles and K-complexes. Sleep spindles, as seen on an EEG recording, are brain wave patterns that begin low in amplitude and gradually increase in amplitude before gradually decreasing over a second or two. Sleep spindles may also be referred to as a crescendo-decrescendo pattern. In general, sleep spindles have a frequency of about 12-14 hertz. K-complexes are brain wave patterns that include large, relatively-slow waves (e.g., 1-2 hertz) and may occur during stage II sleep. During stage III sleep, a subject's brain waves slow further in frequency and may be defined by a period in which delta waves are between 20-50 percent of the total wave patterns. During stage IV sleep, a subject's brain waves slow further still and may be defined by period in which delta waves make up greater than 50 percent of the wave patterns. During REM sleep, a subject's brain waves increase in frequency to the gamma frequency similar to the brain waves observed during waking consciousness.

Further, during REM sleep, various bursts of sawtooth waves may be observed. The sawtooth waves that may be seen during REM sleep may precede a burst of rapid eye movements. Sawtooth waves, as seen on an EEG recording, look like a series of shark fins that oscillate at the theta frequency. Although REM sleep is characterized by actual rapid eye movement, periods of little to no eye movements may occur during REM sleep (tonic REM), which are then punctuated by bursts of rapid eye movement (phasic REM).

Waking consciousness is generally experienced neurophysiologically at a brainwave frequency of about forty hertz. The amygdala is part of the limbic system that judges emotional relevance of an experience. When the amygdala and/or the rest of the limbic system experience an event that has enough emotional relevance, the event is temporarily stored in the hippocampus. A subject's brain hippocampal wave frequency is generally about 3-8 hertz (the theta frequency) when such events are temporarily stored in the hippocampus.

Electrooculography (EOG) records the ocular activity of the electrical potential from the retina, which consists of an electrically-charged nerve membrane. EOG signals can be measured by placing electrodes near an eye. Motion of an eye may cause a measurable change of electrical potential between two or more surface electrodes.

Electromyography (EMG) records the muscular activity of electrical potential across muscular membranes, which range between about 50 microvolts to about 300 millivolts (depending on the muscle under observation). Typical repetition rate of muscle unit firing is about 7 hertz to about 200 hertz, depending on the size of the muscle, the type of muscle, etc. EMG signals may be recorded within a muscle (i.e., intramuscular EMG) or on the surface a subject's skin outside of a muscle.

A subject's EOG and/or EMG may also be useful in determining the sleep cycle of a subject. For example, when phasic burst of EOG eye movements are seen during low EMG activity along with simultaneous low voltage, mixed frequency EEG activity, the subject is likely to be in REM sleep.

Specific brainwave patterns and sleep stages are important for specific types of learning (i.e., learning categories). Specifically, declarative memory such as the recall of learned facts is associated with Slow Wave Sleep, motor procedural memory such as how to ride a bicycle is associated with Slow Wave Sleep and Stage II sleep, and flexible problem solving is associated with REM sleep. Further, blocking specific sleep stages or brainwave patterns impairs memory consolidation for specific types of memory.

More than one sleep stage may be important in learning a task. For instance, learning a finger sequence when playing a piano can result in an increase in both slow waves in Slow Wave Sleep and sleep spindles in Stage II sleep over the part of the cerebral cortex controlling the hand. The brainwave patterns of each sleep stage, the sequential order of sleep stages within a sleep cycle, and the progression of sleep cycles throughout the night are all factors used to affect memory consolidation according to the embodiments and techniques herein.

Additionally, a number of types of reinforcing cues may be presented or re-presented to a subject during sleep (i.e., targeted stimulation). These reinforcing cues may be primary and/or secondary reinforcing cues and may include, by example and not by way of limitation, auditory, visual, olfactory, gustatory, somatosensory, vibrational, proprioceptive, and/or associated with motion, according to embodiments herein. As used herein, the term "primary" is used for consistency of description and may refer to a reinforcing cue that is provided along with a secondary reinforcing cue, or may refer to a reinforcing cue that is not provided along with a secondary reinforcing cue. Sounds (i.e., auditory cues) can be presented in short duration specific to individual facts, relationships, word lists, motor activities, or other learned material, and may be more efficacious for use in targeted memory reactivation. Likewise, visual and somatosensory cues may be specifically provided in controlled durations.

Targeted stimulation may be used for visual or visual imagery reinforcing cues. Enhancing memory recall may be performed by pairing information with visual images as reinforcing cues, as human memory is largely visual in nature. In an example for learning facts, the subject associates each fact to be learned with a visual image, rehearses the pairing, and then rehearses the series of images alone. When recall of the facts is required, the subject recalls the sequence of visual images and then decodes each associated fact that was learned. Use of this method improves recall accuracy for the learned material.

Dual-coding theory postulates that combining verbal associations with visual imagery aids normal learning. Verbal and visual information can represent the same learned material by creating separate representations in both verbal and visual format. For example, the mental concept of a "dog" may be understood as both the word "dog" and as an image of a dog. When asked to recall the stimulus, one can retrieve either the word or the image individually, or both simultaneously. If the word "dog" is recalled, the image or images of prior experiences of dogs will likely be recalled, and if an image of a dog is seen, the word "dog" will likely be recalled. Combining both verbal and visual representations increases the likelihood of accurate memory retrieval. Additionally, verbal and somatosensory associations may be made according to embodiments. For instance, the word "dog" and a tactile application of a stimulus to the hand (e.g., as if petting a dog) of the subject may increase recall.

That is, dual-coding theory is classically described for using verbal associations with visual imagery, but may be used to strengthen the association of auditory and/or somatosensory cues with learned material.

Targeted memory recall and reactivation, according to the described embodiments and techniques, may not only be useful for enhancing learning and memory in normal subjects, but also may be applied to patients with memory disorders such as Alzheimer's disease, Parkinson's disease, vascular dementia, and other disorders of memory impairment.

As noted, human adult sleep typically includes four to five sleep cycles each night where each sleep cycle is about 90 minutes in length. Each sleep cycle contains a sequence of sleep stages normally seen in the order of Stage I, Stage II, slow wave sleep, a second period of Stage II, and then rapid eye movement (REM) sleep. During subsequent sleep cycles, the order repeats itself usually with the omission of Stage I sleep. However, sleep cycles may change in consistency as they progress through the night. The percentage of slow wave sleep is high in the first sleep cycle and wanes during subsequent cycles, while the percentage of REM sleep is low in the first sleep cycle and gradually increases with subsequent cycles.

Specific brainwave patterns and sleep stages may be used according to embodiments for specific types of learning and memory. For example, the brainwave patterns of each sleep stage, the sequential order of sleep stages within a sleep cycle, and the changing consistency of progressive sleep cycles may be used and/or determined for accurate memory consolidation.

For example, in an embodiment, a subject may identify items of material of one or more learning categories to be learned. The subject may then categorize material to be learned into the categories, such as but not limited to: facts, motor skills, or creative thought. In some embodiments, this identification and categorization may be performed by one or more devices, such as a controller apparatus or device described in further detail below. In an illustrative motor skills example, a subject may record or capture motion, sound, and/or biometric data of the subject using cameras, microphones, wearable devices (e.g., a glove or suit to record movement), and later play back the recorded/captured items as a reinforcing cue during sleep.

Primary and secondary reinforcing cues may be selected, paired, and rehearsed with the material to be learned by the subject in order to target the cues to the material. In an embodiment, the primary reinforcing cue is an auditory stimulus, and the secondary reinforcing cue is a visual stimulus or a somatosensory stimulus.

Reinforcing cues (e.g., primary or both primary and secondary) are then re-presented during sleep of the subject, as described herein. Patterns of sleep-related primary reinforcing cue re-presentation that result in accurate post-sleep recall are identified and used to fine-tune future patterns of sleep-related primary reinforcing cue stimulation thus further targeting materials with specific reinforcing cue re-presentation. Secondary reinforcing cues may be provided during sleep in a similar manner to primary reinforcing cues. Primary and secondary reinforcing cues that result in accurate recall are identified and used during future encoding events.

Material to be learned may constitute any form of learning, including reading text, graphs, tables or maps, watching live or prerecorded lectures, television programs, information provided on the Internet, engaging in motor skills, or learning any fact, experience, or relationship encountered during daily experience. Material to be learned may be in any form of sensory (auditory, visual, somatosensory, proprioceptive, rotational, gustatory, or olfactory) information or in the form of a motor skill (musculoskeletal enactment or direct or remote operation of a device or machine), creative thought, and/or the like.

Memory categories may be provided from storage media of a controller device, as described herein, from the Internet or other network, or may be selected by the user and assigned to one of three general categories of facts, motor skills, and creative thought.

The category of facts may include facts, series of facts, historical facts, mathematics, science, language arts, political science, sports, or any other form of declarative knowledge. The category of motor skills may include any motor skill directly enacted by the user such as riding a bicycle, any motor skill indirectly enacted by the user such as direct or remote operation of machinery or devices, or any other motor skill. Motor skills may have both motor and sensory components. The category of creative thought may include music, arts, dance, scientific and commercial innovation, or any other category in which the user wishes to have future creative thoughts or ideas.

Furthermore, subcategories may be designated to categories, e.g., mathematics may be a subcategory of facts. Subcategories may be divided into further subcategories, e.g. mathematics may be subdivided into addition, subtraction, multiplication, division, ratios, geometry, algebra, calculus, linear algebra, discrete mathematics, differential equations, and any other category of mathematics. In a similar fashion the categories of motor skills and creative thought can be subdivided into subcategories which can be further subdivided into additional subcategories as defined by the user.

Accordingly, the techniques and embodiments described herein provide for improvements in memory recall and reactivation by targeted stimulation, as described above.

For instance, methods, systems, devices, and apparatuses are provided for memory recall and reactivation by targeted stimulation. A method in accordance with an example aspect is described. The method is for providing patterns of a reinforcing cue re-presentation during sleep. The method includes receiving an indication of a learning category that a subject has begun to learn by a controller device, and monitoring sleep intervals of the subject while the subject is asleep by a monitoring device. The method also includes determining that the subject is in a specific sleep interval by the controller device, and providing by a stimulation device the reinforcing cue for the learning category to the subject according to one or more patterns during the specific sleep interval based on the subject being in the specific sleep interval.

A method in accordance with another example aspect is described. The method is for determining patterns of a reinforcing cue during sleep. The method includes providing by a stimulation device the reinforcing cue to a subject during a first sleep period for material of a learning category to be learned by the subject according to a first pattern, and receiving by a controller device an indication of accuracy of post-sleep recall of the subject for the material subsequent to the first sleep period. The method also includes determining by the controller device a second pattern for the reinforcing cue to be delivered to the subject during a second sleep period subsequent to the receiving of the indication, the second pattern being determined based on the indication.

A method in accordance with another example aspect is described. The method is for determining reinforcing cues during sleep. The method includes providing by a stimulation device a first reinforcing cue to a subject during learning wakefulness and then during a first sleep period for first material of a learning category to be learned by the subject, and receiving by a controller device an indication of accuracy of post-sleep recall of the subject for the first material subsequent to the first sleep period. The method also includes determining by the controller device a second reinforcing cue to be delivered to the subject during a second sleep period subsequent to the receiving of the indication, the second reinforcing cue being based on the indication.

A method in accordance with another example aspect is described. The method is performed in a sleep system for determining a sleep interval of a subject. The method includes monitoring by a monitoring device of the sleep system for onset of sleep of the subject, and determining by a controller device of the sleep system at least one of a sleep stage of the subject or a sleep cycle of the subject based on the onset of sleep, the onset of sleep being the only monitored aspect of the subject used for determining at least one of the sleep stage of the subject or the sleep cycle of the subject. The method also includes providing a reinforcing cue, according to one or more patterns, to the subject for material of a learning category to be learned by the subject during at least one of a specific sleep stage or a specific sleep cycle based on the subject being in at least one of the specific sleep stage or the specific sleep cycle.

Various example embodiments are described in the following subsections. In particular, example system and device embodiments are described, followed by a description of example operational embodiments. Further example embodiments and advantages are subsequently described, and then example electronic and computing device embodiments are provided. Finally, some concluding remarks are provided. It is noted that the division of the following description generally into subsections is provided for ease of illustration, and it is to be understood that any type of embodiment may be described in any subsection.

III. Example System and Device Embodiments

Systems and devices may be configured in various ways according to the embodiments and techniques described herein. In embodiments, devices and sensors may be operable to form systems for memory recall and reactivation by targeted stimulation. The devices and systems may be configured, according to embodiments, to provide targeted stimulation to a subject as a cue for memory recall and reactivation based on a determined sleep interval of the subject. The devices and systems may be configured, according to embodiments, to provide targeted stimulation, in determined patterns, to a subject as a cue for memory recall and reactivation based on a post-sleep recall accuracy for material learned by the subject using prior patterns. The devices and systems may be configured, according to embodiments, to provide targeted stimulation to a subject as a determined cue for memory recall and reactivation based on a post-sleep recall accuracy for material learned by the subject using prior cues. The devices and systems may be configured, according to embodiments, to determine a sleep interval of a subject based only on a determination of sleep onset of the subject.

Turning now to FIG. 1, a block diagram of a system 100 for memory recall and reactivation by targeted stimulation is depicted. System 100 includes a controller device 102, stimulation device(s) 104, monitoring device(s) 106, and a system backend 108. Controller device 102 and/or system backend 108 may include hardware, logic, and/or software configured to enhance successful memory encoding and recall using targeted memory reactivation by targeted stimulation. Controller device 102 may be communicatively coupled to stimulation device(s) 104, monitoring device(s) 106, and system backend 108 by a connection 110, a connection 112, and a connection 114, respectively. Connection 110, connection 112, and connection 114 may each comprise one or more individual connections according to embodiments, and each individual connection may be a wired or a wireless connection. Connection 114 may be a direct connection or a connection over a network such as a local area network (LAN), the Internet, and/or the like.

Controller device 102 is configured to control stimulation, e.g., targeted stimulation, provided to a subject. Controller device 102 is configured to control stimulation according to one or more of learning categories, stimulation patterns and variations thereof, sleep intervals (e.g., stages, cycles, progressions, etc.), sleep onset, present and/or past post-sleep recall accuracy, stimulation similarities, and/or the like.

Stimulation device(s) 104 is configured to stimulate a subject according to one or more types of stimulation and/or targeted stimulation. Stimulation and/or targeted stimulation may include, by example and not by way of limitation, auditory, visual, olfactory, gustatory, somatosensory, vibrational, proprioceptive, and/or associated with motion, according to embodiments. Stimulation and/or targeted stimulation provided to a subject via stimulation device(s) 104 may be provided as primary or secondary cues in one or more patterns, as described according to techniques and embodiments herein.

Monitoring device(s) 106 is configured to monitor one or more aspects of a subject such as heart data, electrical signal data such as neural activity, motion or movement data, breathing, temperature such as skin temperature or body temperature, pulse rate (i.e., heart rate and its variations) and pulse rate symmetry, and/or the like, as well as any variations thereof. Monitoring device(s) 106 is configured to provide monitored data to controller device 102 via connection 112. Monitoring device(s) 106 may include EEG, EOG, EMG monitoring devices and mechanisms.

System backend 108 is configured to store identification information for a subject, wakefulness information such as learning/memory testing results including post-sleep recall subsequent to stimulation, information from monitoring device(s) 106 and/or stimulation device(s) 104, previously-provided stimulation information, past sleep information including onset, stage, and cycle information, recommended stimulation information, and/or the like. Likewise, such information for other subjects could be collected and/or analyzed by system backend 108 to determine matches for material/learning categories and stimuli (including when applied, patterns applied, etc.). In embodiments, system backend 108 may be a computing device such as a computer or server, or other computing or electronic device described herein, such that system backend 108 includes a processor(s), memory, and storage.

System 100 and its components may be configured to perform its functions in various ways.

In one embodiment, a wearable sensor (see also FIGS. 5 and 19-21 described below), e.g., a motion sensor, such as those described herein, may be utilized as monitoring device(s) 106 and be integrated with an application of a smartphone utilized as controller device 102 having an integrated or externally coupled loudspeaker as stimulation device(s) 104. The wearable sensor may be used to determine sleep and wakefulness of the subject, and the smartphone application may be first used during memory encoding during wakefulness (e.g., memory training), then to provide a primary reinforcing cue re-presentation during sleep of the subject (e.g., an auditory stimulation), and then for post-sleep recall accuracy testing. That is, a subject may use a controller device to learn (i.e., encode memory) and test learning during wakefulness, e.g., using one or more applications running on the controller device.

Fewer components, or additional components as described herein, of system 100 for memory recall and reactivation by targeted stimulation, as shown, may be present in embodiments. Additionally, one or more of stimulation device(s) 104, monitoring device(s) 106, and backend system 108 may be included as a sub-component in controller device 102, as shown in FIG. 2.

Figure 2:
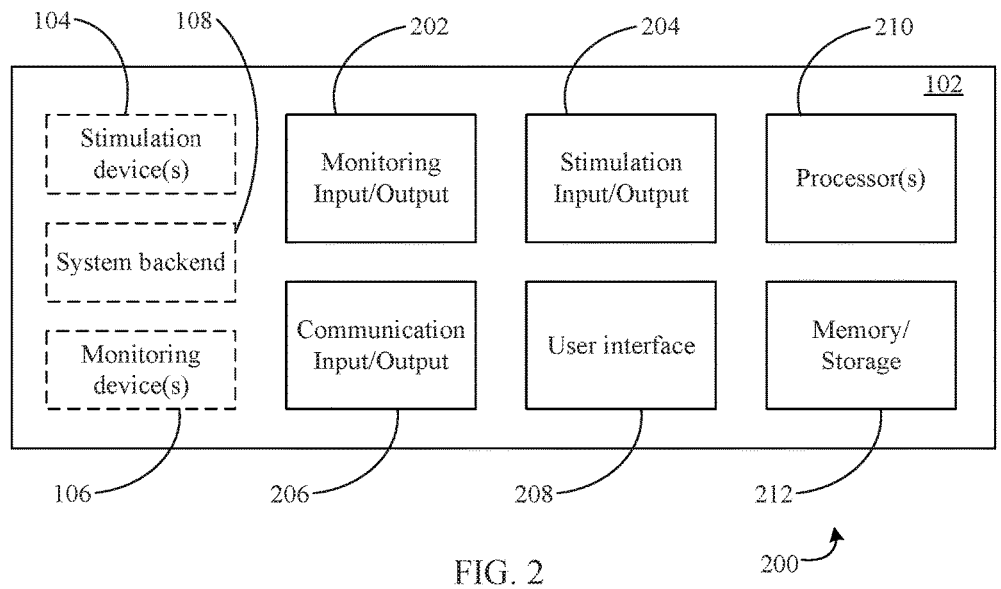
FIG. 2 is a block diagram of a portion of the system for memory recall and reactivation by targeted stimulation of FIG. 1, according to an exemplary embodiment.

FIG. 2 depicts a block diagram of a configuration 200 of controller device 102 of FIG. 1. Configuration 200 of controller device 102 includes a monitoring input/output (I/O) component 202, a stimulation I/O component 204, a communication I/O component 206, a user interface (UI) 208, a processor(s) 210, and a memory/storage 212. As noted above, one or more of stimulation device(s) 104, monitoring device(s) 106, and backend system 108 may be included as a sub-component in controller device 102. The components and devices shown and/or included in configuration 200 may each be communicatively coupled with one or more other components and devices of configuration 200 via communication channels, data buses, wired/wireless connections, and/or the like, not shown for illustrative clarity.

Monitoring I/O component 202 is configured to receive input data from one or more of monitoring device(s) 106. In embodiments, monitoring I/O component 202 may also be configured to provide output data or instructions to one or more of monitoring device(s) 106, such as power commands, feedback data, etc.

Stimulation I/O component 204 is configured to provide output data and/or signals to one or more of stimulation device(s) 104. In embodiments, stimulation I/O component 204 may also be configured to receive input data from one or more of stimulation device(s) 104, such as feedback data, etc.

Communication I/O component 206 is configured to communicate with one or more devices/systems as described herein. Communication I/O component 206 may be configured to communicate via any wireless or wired connection media or protocol, such as but not limited to: Bluetooth™, IEEE 802.11xx, TCP/IP, nearfield and RF, IR, USB, and/or the like. For example, in embodiments, communication I/O component 206 handles the exchange of data and information between controller device 102 and system backend 108 or a network.

User interface (UI) 208 is configured to provide a subject with a mechanism to provide inputs to and receive outputs from controller device 102. In embodiments, UI 208 may be a graphical UI (GUI). In embodiments, user interface 208 may be or include a keypad, a display screen, a touchscreen, one or more buttons, one or more dials, one or more switches, one or more speakers, one or more microphones, etc.

Processor(s) 210 is configured to execute programs and/or instructions to control the operations of controller device 102, to control stimulation device(s) 104, and/or to control monitoring device(s) 106. Processor(s) 210 is also configured to process information received from UI 208, system backend 108, stimulation device(s) 104 and/or monitoring device(s) 106. Processor(s) 210 may be any processor described herein, or the like.

Memory/storage 212 is configured to store data related to a subject, programs and/or instructions to control the operation of controller device 102, information associated with types of stimulus (e.g., primary and secondary cues), information related to one or more subjects including past post-sleep recall data, past and present material/stimulus pairings, etc., and/or the like. In embodiments, memory/storage 212 is configured to provide stored information and data to one or more devices and components of controller device 102, such as processor(s) 210. Memory/storage 212 may be any memory or storage device described herein, or the like.

Figure 3:
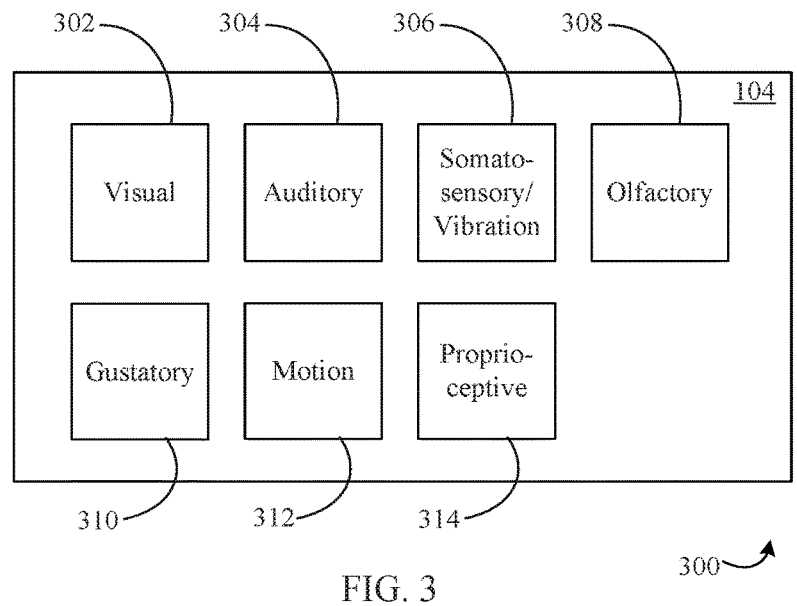
FIG. 3 is a block diagram of a portion of the system for memory recall and reactivation by targeted stimulation of FIG. 1, according to an exemplary embodiment.

FIG. 3 depicts a block diagram of a configuration 300 of stimulation device(s) 104 of FIG. 1. Stimulation device(s) 104 may include a visual stimulation device 302, an auditory stimulation device 304, a somatosensory/vibration stimulation device 306, an olfactory stimulation device 308, a gustatory stimulation device 310, a motion stimulation device 312, a proprioceptive stimulation device 314, and/or the like. In embodiments, stimulation device(s) 104 may be configured to provide targeted stimulation to a subject, including targeted stimulation of varying patterns. Additionally, each of the components and devices of configuration 300 of stimulation device(s) 104 shown in FIG. 3 may comprise one or more of the specific component that may be in varying component types, such as but not limited to, different colored LED lights for visual stimulation device 302, according to embodiments.

Visual stimulation device 302 may comprise one or more lights (e.g., LED lights) or light emitting devices of any color or intensity, a light-emitting mask, goggles or glasses, a display screen such as a computer or television screen, and/or a touchscreen, in embodiments. Visual stimulation device 302 may comprise a plurality lights configured to be presented to a subject and to appear to be from varying parts of the visual field of the subject (i.e., having "directionality"). Auditory stimulation device 304 may comprise one or more loudspeakers that may be wearable (e.g., as in earbuds or headphones) or part of another device described herein, such as controller device 102, in embodiments, and may be configured to provide stimuli with "directionality" characteristics to a subject. Auditory stimulation device 304 may also comprise one or more sound producing mechanisms, such as a device that produces a "click" by physical movement of the device. Somatosensory/vibration stimulation device 306 may comprise clips, wearable patches, bands (e.g., for the fingers, hands, wrist, chest, or head of a subject), or other mechanisms that provide vibrational, touch (e.g., physical contact such as by air movement or device actuation), or temperature stimulus, and/or the like. Somatosensory/vibration stimulation device 306 may be configured to provide stimuli with "directionality" characteristics to a subject. Olfactory stimulation device 308 may comprise a mechanism to produce smells that may be perceived by a subject, e.g., via extracts or solutions and air movement. Gustatory stimulation device 310 may comprise a mechanism to provide tastes that may be perceived by a subject, e.g., via extracts or solutions and provision thereof, e.g., by tube, to taste buds of the subject. Motion stimulation device 312 may include a device or mechanism that provides movement or motion to one or more parts of the body of the subject, e.g., a glove that may be actuated to move fingers of the subject. Proprioceptive stimulation device 314 may include one or more devices or mechanisms configured to produce a stimulation to alter a perceived positional state of the body of the subject.

Figure 4:
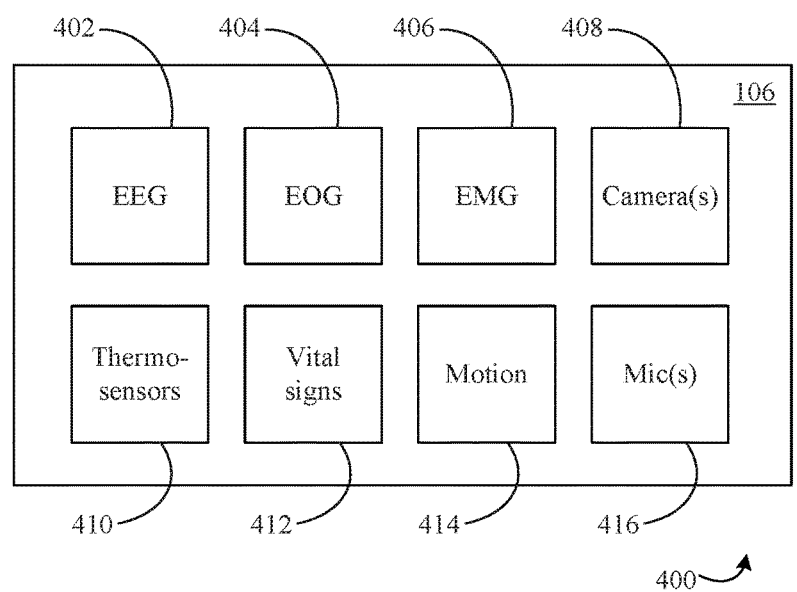
FIG. 4 is a block diagram of a portion of the system for memory recall and reactivation by targeted stimulation of FIG. 1, according to an exemplary embodiment.

FIG. 4 depicts a block diagram of a configuration 400 of monitoring device(s) 106 of FIG. 1. Monitoring device(s) 106 may include an EEG sensor 402, an EOG sensor 404, an EMG sensor 406, a camera 408, a temperature sensor or thermo-sensor 410, a vital sign sensor 412, a motion sensor 414, a microphone (mic) 416, and/or the like. EEG sensor 402 is configured to measure EEG signals of a subject, EOG sensor 404 is configured to measure EOG signals of a subject, and EMG sensor 406 is configured to measure EMG signals of a subject. Temperature sensor or thermo-sensor 410 is configured to measure the temperature of a subject or the environment of the subject, and vital sign sensor 412 is configured to measure one or more vital signs of a subject such as pulse rate/strength, pulse rate symmetry, blood oxygen saturation, blood pressure, etc. Camera 408 is configured to monitor the position and/or movement of a subject, and mic 416 is configured to monitor sounds made by a subject such as breathing sounds including rhythm and/or rate, as well as apneustic breathing sounds.

In embodiments, monitoring device(s) 106 may be configured to monitor aspects of a subject resulting from stimulation by stimulation device(s) 104. Additionally, each of the components and devices of configuration 400 of monitoring device(s) 106 shown in FIG. 4 may comprise one or more of the specific component that may be in varying component types, such as but not limited to, a gyroscope and an accelerometer for motion sensor 414, according to embodiments.

EEG sensor 402, EOG sensor 404, EMG sensor 406, temperature sensor or thermo-sensor 410, and vital sign sensor 412 may include electrodes or other sensors affixed to the subject by bands, adhesives, or patches, or may include a mechanical attachment mechanism such as an encasement or clip, e.g., a finger clip. Motion sensor 414 may include one or more accelerometers and/or gyroscopes, and may be included in a wearable device in embodiments. Microphone 416 may comprise one or more microphones including a directional microphone array to detect sounds from a specific area of a subject or environment. Camera 408 may include one or more infrared cameras and/or standard motion cameras, or other types of cameras including wearable cameras or cameras included in devices described herein (e.g., included in controller device 102).

The embodiments described in this subsection may be adapted to any wearable electronic devices and/or sensors, as well as communication devices and computing devices, as described herein.

IV. Example Operational Embodiments

The embodiments described herein may perform their functions in various ways for memory recall and reactivation by targeted stimulation. The embodiments described in this subsection may be adapted to any wearable electronic devices and/or sensors, as well as communication devices and computing devices, as described herein.

In embodiments, a subject may activate controller device 102 (of FIGS. 1 and 2) that is executing a software program to identify and categorize individual items of material to be learned. The subject may interact with the program via UI, as described above, such as a touchscreen for mobile devices, or such as a keyboard/mouse for computers.

After the subject identifies and categorizes individual items of material to be learned, the subject selects primary (and secondary, if desired) reinforcing cues and pairs them to specific items of the material. In embodiments, the most efficacious form of a primary reinforcing cue may be auditory, and the most efficacious form of a secondary reinforcing cue may be visual or somatosensory. Auditory reinforcing cues may include any sound or sounds derived from provided media, the Internet, or personal media perceived by the human auditory system, or any other sound(s) described herein. Visual reinforcing cues may include any visual representation(s) derived from text or characters, provided media, the Internet, or personal media perceived by the human visual system, or any other visual content described herein.

Reinforcing cues may also be in the form of any sensory modality including somatosensory, proprioceptive, rotational, gustatory, or olfactory sensory information, or any others described herein.

When the subject is ready for memory encoding, i.e., memory training to learn material, the subject activates the assigned primary reinforcing cue immediately before or simultaneously with presentation of the material to be learned, e.g., by activating a function of controller device 102. This pairing may be rehearsed as deemed necessary by the subject. Alternatively, the user selects both primary and secondary reinforcing cues and pairs them to specific items of material to be learned, exploiting the dual-coding theory, in order to strengthen the association of the primary reinforcing cue with the material to be learned.

In embodiments, controller device 102, by execution of the software program, may cause the assigned primary reinforcing cue to be presented to the subject immediately before or simultaneously with presentation, by controller device 102, of the material to be learned The primary reinforcing cue is then re-presented to the subject during sleep.

For example, as noted above, in one embodiment, a wearable device or sensor, e.g., a motion sensor, such as those described herein may be utilized as monitoring device(s) 106 and be integrated with an application of a smartphone utilized as controller device 102 having an integrated or externally coupled loudspeaker as stimulation device(s) 104. The wearable sensor may be used to determine sleep and wakefulness of the subject, and the smartphone application may be first used during memory encoding during wakefulness (e.g., training), or prior testing, then to provide a primary reinforcing cue re-presentation during sleep of the subject (e.g., an auditory stimulation), and then for post-sleep recall.

Figure 5:
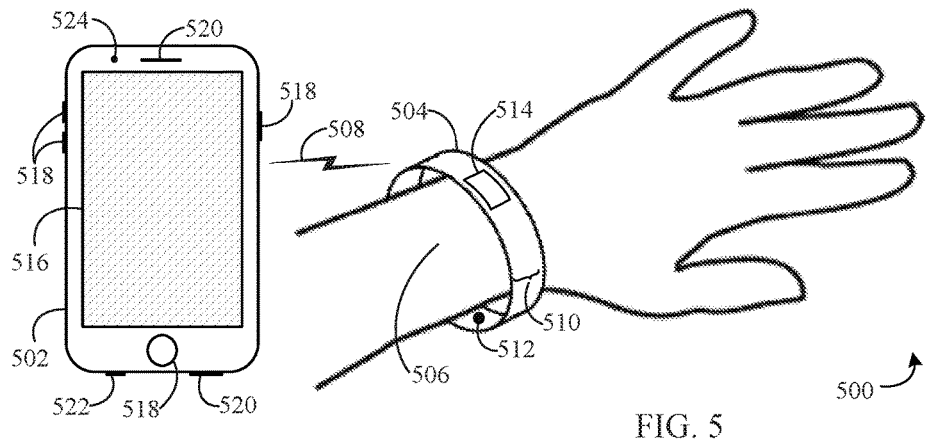
FIG. 5 is a diagram of an implementation of the system for memory recall and reactivation by targeted stimulation, according to an exemplary embodiment.

FIG. 5 is a diagram of an exemplary system 500 for providing targeted stimulation for memory recall and reactivation. System 500 includes a controller device 502 and a monitoring device 504 that is wearable on a wrist of a subject 506. Controller device 502 and monitoring device 504 are communicatively coupled via a wireless connection 508, according to any wireless connectivity described herein (though wired connections are also contemplated). Controller device 502 may be a mobile device, computer, processing device, electronic device, etc., as described herein, and monitoring device 504 may be one or more sensors or a wearable device, as described herein. As shown for illustration, controller device 502 is a smart phone and monitoring device 504 is an electronic device such as one of a wearable fitness monitoring device described herein.

Monitoring device 504 may be a further embodiment of monitoring device(s) 106 of FIGS. 1 and 4. Monitoring device 504 includes a wearable band 510, one or more sensors 512, and a control unit 514. One or more sensors 512 may be affixed to, or be part of, wearable band 510 and may be one or more of the sensors described herein. Control unit 514 may be affixed to or part of wearable band 510 and may include a processing device or processing circuitry, a memory, communication circuitry, a UI, a display, a speaker(s), a vibration component, and/or the like. In embodiments, control unit 514 is configured to provide information monitored by one or more sensors 512, and that relates to one or more aspects of subject 506, to controller device 502.

Controller device 502 includes a touchscreen 516, buttons 518, speakers 520, a microphone (mic) 522, a camera 524, as well as a processor, memory/storage, a vibration component, and/or communication circuitry (not shown) as would understood by persons skilled in the relevant art(s) having the benefit of this disclosure. In embodiments, controller device 502 is configured to execute a software program to allow subject 506 to identify and categorize individual items of material to be learned by subject 506.

Subject 506 may interact with controller device 502 and the program via a UI such as touchscreen 516 and/or buttons 518. In embodiments, subject 506 may interact with controller device 502 and the program via voice commands provided to mic 522.

Subsequent to subject 506 identifying and categorizing the material to be learned, subject 506 may select primary (and secondary, if desired) reinforcing cues, and pair them to specific items of the material by interacting with controller device 502 as described herein. For example, in the described embodiment, an auditory reinforcing cue may be the primary cue and a visual reinforcing cue may be the secondary cue. The auditory and visual reinforcing cues may be stored in or streamed by controller device 502. As noted above, however, reinforcing cues may also be in the form of any sensory modality including somatosensory, proprioceptive, rotational, gustatory, or olfactory sensory information, or any others described herein.

Subject 506 may begin memory encoding, i.e., memory training to learn material, by activating the assigned primary reinforcing cue (or both primary and secondary reinforcing cues) immediately before or simultaneously with presentation of the material to be learned. In embodiments, controller device 502 may cause the assigned primary reinforcing cue to be presented to the subject immediately before or simultaneously with presentation, by controller device 102, of the material to be learned In embodiments, the functionality described with respect to controller device 502 may be present in monitoring device 504, e.g., in control unit 514.

The reinforcing cue(s) is then re-presented to subject 506 during sleep as described in further detail below.

A. Reinforcing Cues Based on Sleep Interval

According to embodiments, primary and second reinforcing cues may be presented (or re-presented) to a subject in one or more patterns during certain sleep intervals based on material to be learned. That is, the techniques and embodiments herein provide for monitoring aspects of a subject, determining a specific sleep interval of the subject, and providing targeted stimulation as primary and/or second reinforcing cues.

Sleep intervals, e.g., sleep stages, sleep cycles, progressions of sleep stages within a sleep cycle, and progressions of sleep cycles throughout a sleep period, as well as specific sleep activity having a duration such as production of sleep spindles or K-complexes, may be determined by EEG, EOG, EMG, heart rate variability, actigraphy, motion sensors, position sensors, or any other modality described herein that may be used to determine sleep, sleep-related neurophysiologic waveforms, sleep stages, and sleep cycles. Sleep stages and sleep cycles may also be predicted based on sleep onset time in combination with data indicating the circadian rhythmicity of the subject, using actigraphy, motion sensors, or other measurements of activity used to predict sleep and wakefulness. Sleep stages and sleep cycles may also be predicted using sleep onset time alone.

Figure 6:
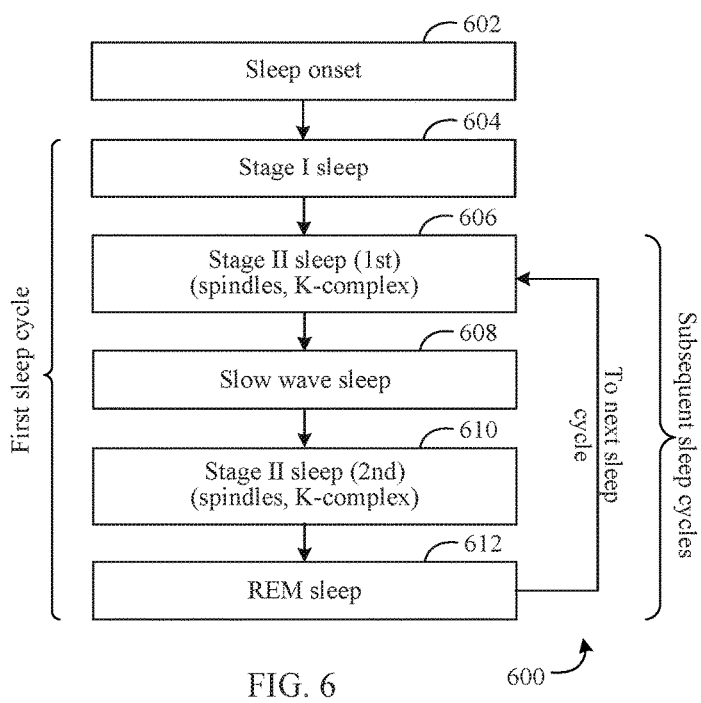
FIG. 6 is a flowchart of sleep intervals, e.g., sleep stages, sleep cycles, progressions of sleep stages within a sleep cycle, and progressions of sleep cycles throughout a sleep period, as well as specific sleep activity having a duration such as production of sleep spindles or K-complexes, according to an exemplary embodiment.

FIG. 6 is a flowchart 600 depicting example sleep intervals. Flowchart 600 is described as follows.

Flowchart 600 begins with stage 602. In stage 602, a subject experiences an onset of sleep. Sleep onset, as in state 602, may be determined as described in further detail below.

In state 604, the subject enters Stage I sleep. Subjects may enter Stage I sleep immediately after sleep onset (state 602). As noted above, Stage I sleep is a characterized by a subject's brain waves slowing in frequency and transitioning from alpha waves to theta waves. Stage I sleep is frequently present in the first sleep cycle of a subject's time asleep as the first sleep state, and is often not present in subsequent sleep cycles.

In state 606, the subject enters Stage II sleep. In Stage II sleep, brain waves further slow in frequency relative to Stage I sleep. Sleep spindles and K-complex waveforms may be produced during Stage II sleep. Stage II sleep represented in state 606 is the first instance of Stage II sleep in a given sleep cycle.

In state 608, the subject enters slow wave sleep (Stages III-IV). In slow wave sleep, brain waves further slow in frequency relative to Stage II sleep and waves are comprised of delta waves between 20% and 50% (Stage III) or greater than 50% (Stage IV).

In state 610, the subject enters Stage II sleep for a second time during a sleep cycle. Stage II sleep represented in state 610 is a relatively short sleep state between states 608 and 612.

In state 612, the subject enters REM sleep. REM sleep includes brain waves that increase in frequency and is characterized by production of beta and gamma waves and rapid eye movement of the subject that may be preceded by bursts of sawtooth waves. REM sleep is the final sleep state in a given sleep cycle.

From state 612, after a sleep cycle completes, the state may return to state 606 to begin a subsequent sleep cycle.

Patterns of primary reinforcing cue re-presentation during sleep may be directed by the categorical assignment of material to be learned to different learning categories such as facts, motor skills, and creative thought, and may take place during specific sleep intervals.

For instance, primary reinforcing cues paired with items of material to be learned in the category of facts may be re-presented during slow wave sleep. Primary reinforcing cues paired with items of material to be learned in the category of motor skills may be preferentially re-presented during slow wave sleep and Stage II sleep. Primary reinforcing cues paired with items of material to be learned in the category of creative thought may be preferentially re-presented during REM sleep. According to embodiments, reinforcing cues may be presented during only the sleep intervals described in this paragraph. However, in other embodiments, reinforcing cues of any category may be re-presented during any sleep state (e.g., sleep stage, sleep cycle, combinations of sleep stages or cycles, progressions, sleep spindle or K-complex production, etc.).

Figure 7:
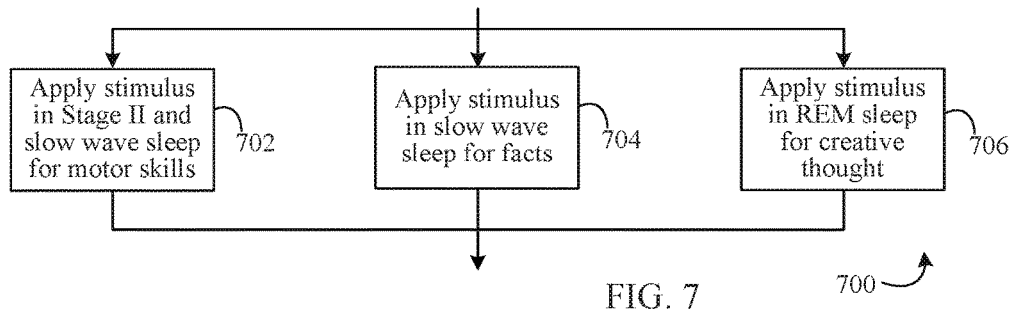
FIG. 7 is a flowchart for applying targeted stimuli for learning categories by sleep intervals, according to an exemplary embodiment.

FIG. 7 is a flowchart 700 providing example steps for providing patterns of a primary reinforcing cue re-presentation during sleep, according to an exemplary embodiment. Configuration 100 of FIG. 1, system 500 of FIG. 5, and/or any of their respective components/circuits may each operate according to flowchart 700, in embodiments. Other structural and operational embodiments will be apparent to persons skilled in the relevant art(s) based on the discussion regarding flowchart 700. Flowchart 700 is described as follows.

Flowchart 700 comprises step 702, step 704, and step 706.

In step 702, a stimulus is applied in Stage II and slow wave sleep as a reinforcing cue for material in a motor skills learning category. For example, a reinforcing cue for motor skills material being learned by a subject may be provided to the subject in state 606, state 608, and/or state 610 of flowchart 600, in one or more sleep cycles.

In step 704, a stimulus is applied in slow wave sleep as a reinforcing cue for material in a facts learning category. For example, a reinforcing cue for factual material being learned may be provided to the subject in state 608 of flowchart 600, in one or more sleep cycles.

In step 706, a stimulus is applied in REM sleep as a reinforcing cue for material in a creative thought learning category. For example, a reinforcing cue for creative thoughts material being learned by a subject may be provided to the subject in state 612 of flowchart 600, in one or more sleep cycles.

During a given sleep cycle, one or more of step 702, step 704, and step 706 may be performed for material of different learning categories, according to embodiments.

Figure 8:
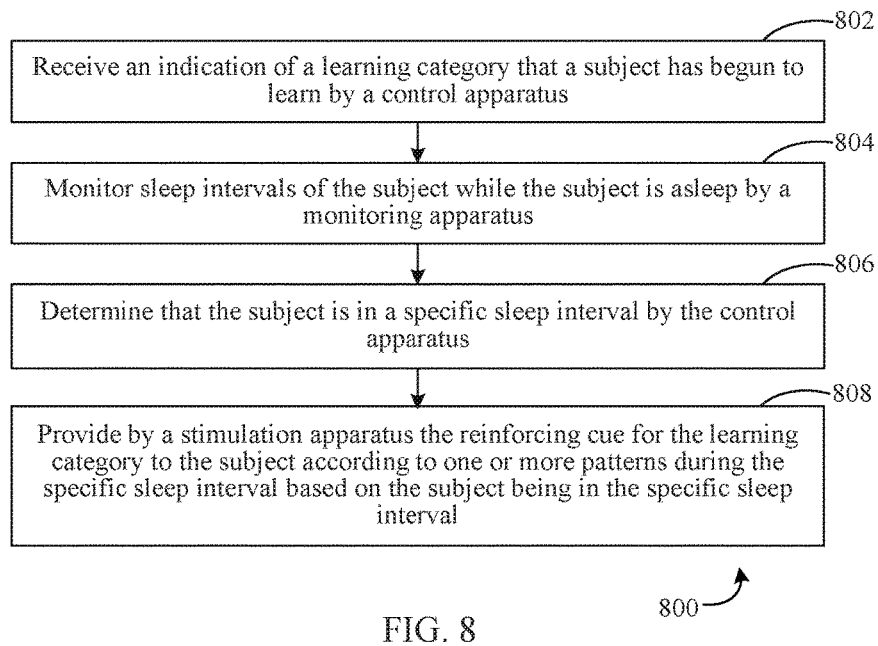
FIG. 8 is a flowchart for providing patterns of a primary reinforcing cue re-presentation during sleep, according to an exemplary embodiment.

Turning now to FIG. 8, a flowchart 800 providing example steps for providing patterns of a reinforcing cue re-presentation during sleep is provided, according to an exemplary embodiment. Flowchart 800 may be a further embodiment of flowchart 700 of FIG. 7. Configuration 100 of FIG. 1, system 500 of FIG. 5, and/or any of their respective components/circuits may each operate according to flowchart 800, in embodiments. In embodiments, controller device 102 and controller device 502 are configured to execute a software program to allow a subject to identify and categorize individual items of material to be learned by the subject. Other structural and operational embodiments will be apparent to persons skilled in the relevant art(s) based on the discussion regarding flowchart 800. Flowchart 800 is described as follows.

Flowchart 800 may begin with step 802. In step 802, an indication of a learning category that a subject has begun to learn is received by a controller device. In embodiments, controller device 102 of FIGS. 1 and 2 or controller device 502 of FIG. 5 may receive an indication of a learning category that a subject has begun to learn. For example, a subject (e.g., subject 506 of FIG. 5) may interact with controller device 502 and the program via a UI such as touchscreen 516 and/or buttons 518 to identify and categorize individual items of material to be learned by subject 506. In embodiments, the program may present selectable options for material to be learned by subject 506 via touchscreen 516. Such selectable options may be for new material, previously-learned material, or material related to previously-learned material (e.g., a subsequent chapter of mathematics coursework being learned by the subject). The subject may then pair the material with a primary reinforcing cue, such as an auditory cue, as well as a secondary reinforcing cue. In an example where the subject is learning the primary colors (i.e., where the category is facts), the auditory cue may include sounds of the names of the primary colors, or may simply include sounds for the word "colors" or the word "color."

In step 804, sleep intervals of the subject are monitored while the subject is asleep by a monitoring device. In embodiments, monitoring device(s) 106 of FIGS. 1 and 4 or monitoring device 504 of FIG. 5 may monitor the sleep intervals of the subject. For example, aspects of the subject such as heart/pulse rate, pulse rate symmetry, EEG/EOG/EMG activity, motion, or other aspects disclosed herein may be monitored by monitoring device(s) 106 of FIGS. 1 and 4 (using EEG sensor 402, EOG sensor 404, EMG sensor 406, camera 408, temperature sensor or thermo-sensor 410, vital sign sensor 412, motion sensor 414, or microphone (mic) 416 of FIG. 4) or monitoring device 504 of FIG. 5 (using one or more sensors 512 of FIG. 5). In embodiments, heart/pulse rate variability and/or symmetry thereof may be monitored by vital sign sensor 412, ocular activity may be monitored by EOG sensor 404, or neural activity may be monitored by EEG sensor 402, and information regarding the monitored aspects is proved to controller device 102 or controller device 502.

In step 806, it is determined that the subject is in a specific sleep interval by the controller device. In embodiments, controller device 102 of FIGS. 1 and 2 or controller device 502 of FIG. 5 may determine that the subject is in a specific sleep interval based on information provided by monitoring devices monitoring device(s) 106 or monitoring device 504 in step 804. A pulse/heart rate (including variability and symmetry), ocular activity, or neural activity associated with a sleep interval may be determined by controller device 102 or controller device 502. For example, on receiving information indicating production of sleep spindles or K-complexes, or brain waves comprising delta waves, it may be determined that the subject is in Stage II sleep. Likewise, from information received that indicates increased levels ocular activity, it may be determined that the subject is in REM sleep. Similarly, received pulse information may be used to determine a corresponding sleep interval.

In step 808, the reinforcing cue for the learning category is provided by a stimulation device to the subject according to one or more patterns during the specific sleep interval based on the subject being in the specific sleep interval. In embodiments, stimulation device(s) 104 of FIGS. 1 and 3, controller device 102 of FIGS. 1 and 2 or controller device 502 of FIG. 5, or control unit 514 of monitoring device 504 of FIG. 5 may provide the reinforcing cue stimulus to the subject. For instance, a light, a sound, or a vibration may be provided by control unit 514 or by controller device 102 or controller device 502. Likewise, visual stimulation device 302, auditory stimulation device 304, somatosensory/vibration stimulation device 306, olfactory stimulation device 308, gustatory stimulation device 310, motion stimulation device 312, or proprioceptive stimulation device 314 of FIG. 3 may provide one or more respective stimuli. The provision of the primary reinforcing cue may be triggered by controller device 102 or controller device 502 based on the determination of sleep interval in step 806.

Continuing with the primary colors example provided above, and in the context of FIG. 5, controller device 502 may determine that subject 506 is in Stage II sleep (as described according to steps 804 and 806). As noted above in step 802, controller device 502 receives an indication that material of the facts learning category was learned by subject 506. Thus, controller device 502 may provide the reinforcing cue to subject 506 during Stage II sleep (for facts) by providing an auditory stimulus via speakers 520 (or a paired external speaker not shown) or by providing a visual stimulus via touchscreen 516. For instance, speakers 520 may provide sound for the word "color" or "colors," or touchscreen 516 may activate to provide white light or light in one or more of the primary colors. In alternate embodiments, controller device 502 may vibrate in the proximity of subject 506

The provision of the reinforcing cue stimulus may be according to one or more patterns, in embodiments. For example, the word "color" may be repeated (e.g., a frequency pattern element) at a given volume after a determined interval of silence during Stage II sleep. Similarly, light may be presented at a given intensity for a determined amount of time that is followed by an interval of no light being presented. Patterns such as these may be repeated during given sleep interval or across multiple sleep intervals. Patterns and attributes thereof may be varied to improve memory recall and reactivation and stimulation efficacy, as described in further detail below.

In some example embodiments, one or more of steps 802, 804, 806, and/or 808 of flowchart 800 may not be performed. Moreover, steps in addition to or in lieu of steps 802, 804, 806, and/or 808 may be performed. Further, in some example embodiments, one or more of steps 802, 804, 806, and/or 808 may be performed out of order, in an alternate sequence, or partially (or completely) concurrently with other steps.

B. Determining Reinforcing Cues

Reinforcing cues for re-presentation during sleep of a subject may be modified or changed to increase memory recall and reactivation efficacy. For example, reinforcing cues for re-presentation during sleep may be matched with post-sleep recall accuracy, according to embodiments. Cues resulting in high recall accuracy may be repeated during future sleep-related stimulation events while cues resulting in poor recall accuracy are not. Cues may be further modified or changed as more recall accuracy data is acquired. In embodiments, the matching of cues to accuracy may be performed by a subject, or may be automatically performed by a device, such as controller device 102 or controller device 502 described herein. Cues may also be modified according to user preference or self-reporting of post-sleep recall accuracy.

Figure 9:
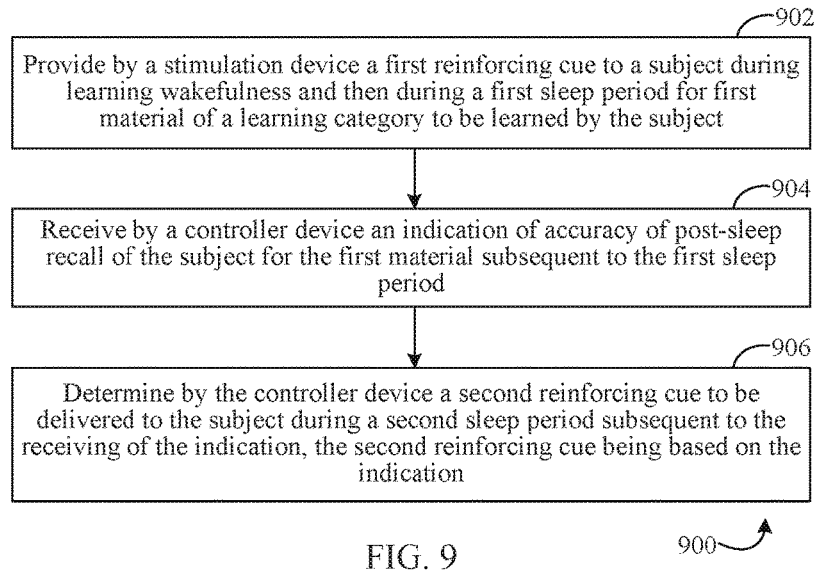
FIG. 9 is a flowchart for determining primary reinforcing cues during sleep, according to an exemplary embodiment.

FIG. 9 is a flowchart 900 providing example steps for determining reinforcing cues during sleep, according to an exemplary embodiment. Configuration 100 of FIG. 1, system 500 of FIG. 5, and/or any of their respective components/circuits may each operate according to flowchart 900, in embodiments. In embodiments, controller device 102 and controller device 502 are configured to execute a software program to allow a subject to identify and categorize individual items of material to be learned by the subject. Other structural and operational embodiments will be apparent to persons skilled in the relevant art(s) based on the discussion regarding flowchart 900. Flowchart 900 is described as follows.

Flowchart 900 may begin with step 902. In step 902, a first reinforcing cue is provided by a stimulation device to a subject during learning wakefulness and then during a first sleep period for first material of a learning category to be learned by the subject. In embodiments, stimulation device(s) 104 of FIGS. 1 and 3 or controller device 502 of FIG. 5 may provide a reinforcing cue to a subject during sleep for material of a learning category that the subject has begun to learn. For instance, a light, a sound, or a vibration may be provided by control unit 514 or by controller device 102 or controller device 502. Likewise, visual stimulation device 302, auditory stimulation device 304, somatosensory/vibration stimulation device 306, olfactory stimulation device 308, gustatory stimulation device 310, motion stimulation device 312, or proprioceptive stimulation device 314 of FIG. 3 may provide one or more respective stimuli. The provision of the reinforcing cue may be triggered according to embodiments described herein.

As an example, consider the above-described learning scenario in which a subject is learning the primary colors in the context of FIG. 5. During a first period of sleep, subject 506 is provided with a first reinforcing cue that comprises an auditory stimulus: sounds for the word "color." The first reinforcing cue is provided by controller device 502 of FIG. 5 to subject 506 via speakers 520.

In step 904, an indication of accuracy of post-sleep recall of the subject for the first material subsequent to the first sleep period is received by a controller device. In embodiments, controller device 102 of FIGS. 1 and 2 or controller device 502 of FIG. 5 may receive an indication of accuracy of post-sleep recall of the subject. For instance, the subject may test their post-sleep recall of the material for which the first reinforcing cue was provided in step 902. The testing may take place during a period of wakefulness of the subject subsequent to the first period of sleep in step 902, such as immediately or substantially immediately after waking. In embodiments, the testing may take place offline, and the subject may provide results to controller device 102 or controller device 502 through interaction with the devices. In embodiments, the testing may be administered and/or reported by a testing proctor or other person. In other embodiments, controller device 102 or controller device 502 may provide the post-sleep recall test to the subject and receive answers to the test from the subject to determine an indication of accuracy. In still other embodiments, a user may be tested by, or provide an indication of accuracy to, a portion of a system backend (e.g., system backend 108 of FIG. 1) which may in turn provide the indication of accuracy to controller device 102 or controller device 502.

Continuing the learning example for primary colors, subject 506 is tested on material for the primary colors. In this example, subject 506 is tested for post-sleep recall of the material during the first period of wakefulness subsequent to the first sleeping period of step 902. Subject 506 may input answers to the test of post-sleep recall directly into controller device 102 or controller device 502, or an indication of accuracy may be provided to, and received by, controller device 102 or controller device 502 in another manner, such as those described herein. According to embodiments, the post-sleep recall test may result in a first accuracy that is at or above a threshold related to high levels of efficacy, or may result in a second accuracy that is below the threshold. In embodiments, the threshold value may be stored by controller device 102 or controller device 502 for making a determination, e.g., by comparison, of accuracy level to threshold.

In step 906, a second reinforcing cue to be delivered to the subject during a second sleep period subsequent to the receiving of the indication is determined by the controller device, the second reinforcing cue being based on the indication. In embodiments, controller device 102 of FIGS. 1 and 2 or controller device 502 of FIG. 5 may determine a second reinforcing cue to be delivered to the subject during a sleep period subsequent to receiving the indication of accuracy for the post-sleep recall test in step 904. For instance, another light, sound, or vibration may be determined to be provided by controller device 102 or controller device 502 (or by control unit 514 in embodiments).

In some embodiments, the second reinforcing cue may be the same or substantially similar as the first reinforcing cue. That is, if the post-sleep recall accuracy determined in step 904 is at or above the threshold, memory recall and reactivation with targeted stimulation is high, and the first reinforcing cue stimulation should be maintained and re-presented in future sleep periods. On the other hand, if the post-sleep recall accuracy determined in step 904 is below the threshold, memory recall and reactivation with targeted stimulation is low, and the first reinforcing cue stimulation should be changed to a different cue for presentation during encoding periods and for re-presented in future sleep periods. The provision of the second reinforcing cue may be triggered according to embodiments described herein.

Continuing with the primary colors learning example, and in the context of FIG. 5, controller device 502 may determine that post-sleep recall accuracy is below a desired level. For instance, when the subject is learning red, yellow, and blue as the primary colors, the reinforcing cue is the sound of the word "color," and the subject expects a post-recall accuracy of better than 50% (the threshold value may be set to two correct answers), a single correct answer (i.e., 1 out of 3, or 33% accuracy) during post-sleep recall testing would be an indication of accuracy below the threshold, and controller device 502 determines a new, second reinforcing cue to be used. If the accuracy exceeds the threshold (e.g., 2 or 3 correct answers; 66% or 100% accuracy), controller device 502 determines the first reinforcing cue should continue to be used. However, in embodiments, after a specified number of encoding/learning sessions and reinforcement sleep sessions, the threshold may be raised to where all correct answers (e.g., mastery of the material) is desired, and controller device 502 may then determine that a new reinforcing cue should be used if mastery is not yet achieved.

In embodiments, when controller device 502 determines that a different, second reinforcing cue should be used, it may be determined that that a different type of reinforcing cue should be used (e.g., visual instead of auditory), or that a different stimulus of the same type should be used (e.g., using sounds of the words "red," "yellow," and "blue" in the same order the colors are encoded instead of only the sound of the word "color").

The determination of what the second reinforcing cue should be may be based on data/information from past encoding/recall testing of the subject or of other subjects (e.g., as obtained from a system backend such as system backend 108), may be based on other descriptive attributes related to the material and/or learning category (e.g., a yellow light instead of a sound of the word "yellow" or a sound of a cat meowing instead of a sound of the word "cat"), or may be determined based on input by the subject.

Figure 10:
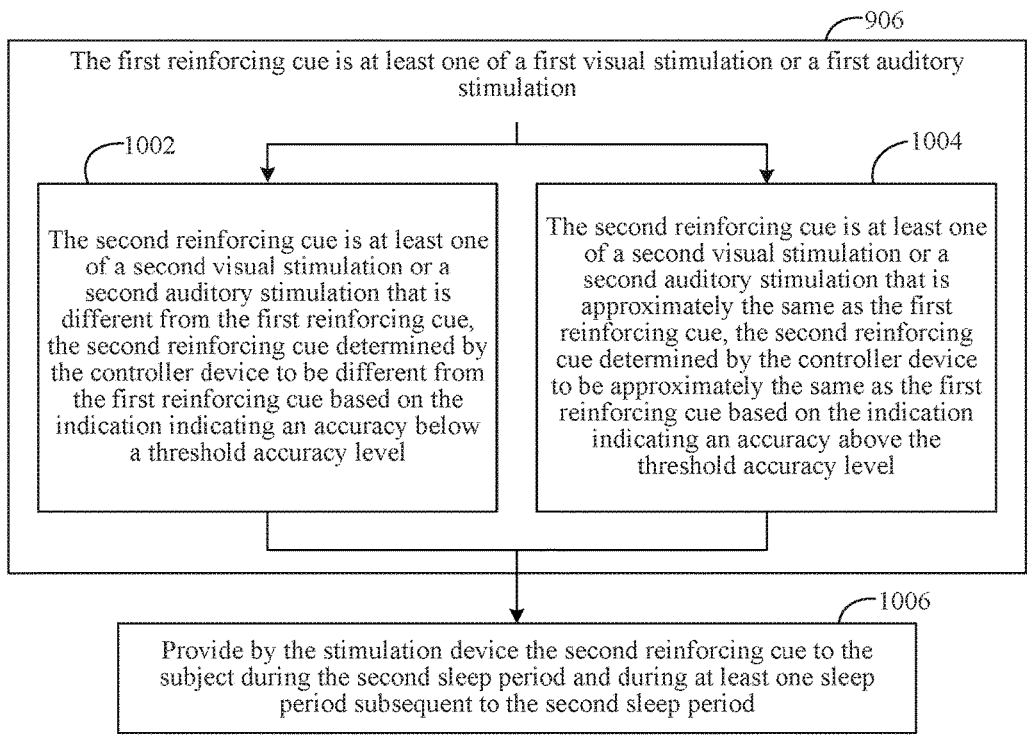
FIG. 10 is a flowchart for determining primary reinforcing cues during sleep, according to an exemplary embodiment.

For instance, FIG. 10 is a flowchart 1000 providing example steps for determining second reinforcing cues, according to an exemplary embodiment. Configuration 100 of FIG. 1, system 500 of FIG. 5, and/or any of their respective components/circuits may each operate according to flowchart 1000, in embodiments. Flowchart 1000 may be a further embodiment of step 906 of flowchart 900 of FIG. 9 in which a second reinforcing cue is determined. Other structural and operational embodiments will be apparent to persons skilled in the relevant art(s) based on the discussion regarding flowchart 1000. Flowchart 1000 is described as follows.

In flowchart 1000, in the context of flowchart 900, the first reinforcing cue may be at least one of a first visual stimulation or a first auditory stimulation. In embodiments, flowchart 1000 may alternatively proceed through step 1002 or step 1004 to step 1006.

In step 1002, the second reinforcing cue is at least one of a second visual stimulation or a second auditory stimulation that is different from the first reinforcing cue, the second reinforcing cue being determined by the controller device to be different from the first reinforcing cue based on the indication indicating an accuracy below a threshold accuracy level. In embodiments, as noted above, controller device 502 (or controller device 102) may determine that a new, different reinforcing cue is to be used when the accuracy of post-sleep recall of the subject is below a threshold.

In step 1004, the second reinforcing cue is at least one of a second visual stimulation or a second auditory stimulation that is approximately the same as the first reinforcing cue, the second reinforcing cue being determined by the controller device to be approximately the same as the first reinforcing cue based on the indication indicating an accuracy above the threshold accuracy level. In embodiments, as noted above, controller device 502 (or controller device 102) may determine that the first reinforcing cue, or a cue that is approximately the same, i.e., substantially similar, is to be maintained and used when the accuracy of post-sleep recall of the subject is at or above the threshold.

In step 1006, the second reinforcing cue is provided by the stimulation device to the subject during the second sleep period and during at least one sleep period subsequent to the second sleep period. In embodiments, stimulation device(s) 104 of FIGS. 1 and 3 or controller device 502 of FIG. 5 may provide a second reinforcing cue to the subject during following sleep periods, such as the next two sleep periods immediately following the determination of the second reinforcing cue in step 906. Second reinforcing cues may be provided by control unit 514 or by controller device 102 or controller device 502, and/or by visual stimulation device 302, auditory stimulation device 304, somatosensory/vibration stimulation device 306, olfactory stimulation device 308, gustatory stimulation device 310, motion stimulation device 312, or proprioceptive stimulation device 314 of FIG. 3. The provision of the second reinforcing cue may be triggered according to embodiments described herein.

As an illustrative example, consider again the primary color learning scenario. Subject 506 is provided with a first reinforcing cue that comprises an auditory or visual stimulus during sleep. During post-sleep recall testing on Thursday morning, the accuracy of recall is determined, and controller device 502 receives an indication that the accuracy is below the desired threshold. Controller device determines a different, second reinforcing cue based on the indication of the accuracy. The second reinforcing cue is provided by controller device 502 of FIG. 5 to subject 506 during two subsequent sleep periods, e.g., Thursday night and Friday night, or Thursday afternoon (nap) and Thursday night.

In some example embodiments, one or more of steps 1002, 1004, and/or 1006 of flowchart 1000 may not be performed. Moreover, steps in addition to or in lieu of steps 1002, 1004, and/or 1006 may be performed. Further, in some example embodiments, one or more of steps 1002, 1004, and/or 1006 may be performed out of order, in an alternate sequence, or partially (or completely) concurrently with other steps.

Referring back to flowchart 900, the provision of a reinforcing cue stimulus may be according to one or more patterns, in embodiments.

In some example embodiments, one or more of steps 902, 904, and/or 906 of flowchart 900 may not be performed. Moreover, steps in addition to or in lieu of steps 902, 904, and/or 906 may be performed. Further, in some example embodiments, one or more of steps 902, 904, and/or 906 may be performed out of order, in an alternate sequence, or partially (or completely) concurrently with other steps.

Figure 11:
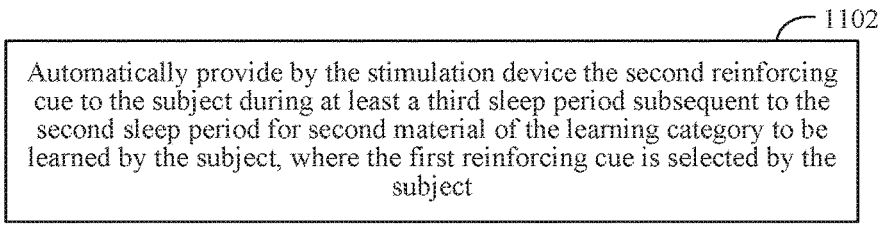
FIG. 11 is a flowchart for determining primary reinforcing cues during sleep, according to an exemplary embodiment.
Figure 12:
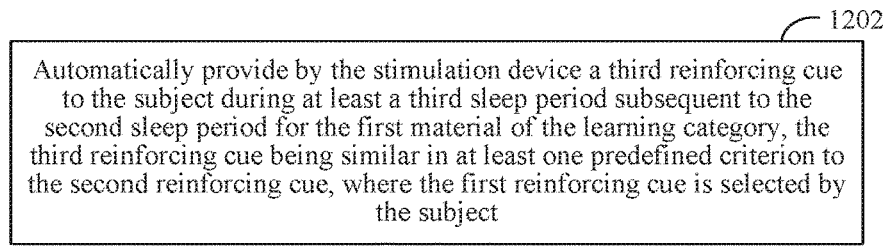
FIG. 12 is a flowchart for determining primary reinforcing cues during sleep, according to an exemplary embodiment.

FIG. 11 is a flowchart 1100 and FIG. 12 is a flowchart 1200, each providing example steps for providing additional reinforcing cues, according to exemplary embodiments. Configuration 100 of FIG. 1, system 500 of FIG. 5, and/or any of their respective components/circuits may each operate according to flowchart 1100 and flowchart 1200, in embodiments. Flowchart 1100 and flowchart 1200 may be further embodiments of flowchart 1000 of FIG. 10. Other structural and operational embodiments will be apparent to persons skilled in the relevant art(s) based on the discussion regarding flowcharts 1100 and 1200.

In embodiments, with respect to flowcharts 1100 and 1200, stimulation device(s) 104 of FIGS. 1 and 3 (e.g., visual stimulation device 302, auditory stimulation device 304, somatosensory/vibration stimulation device 306, olfactory stimulation device 308, gustatory stimulation device 310, motion stimulation device 312, or proprioceptive stimulation device 314), controller device 102 of FIG. 1, and/or control unit 514 or controller device 502 of FIG. 5 may provide reinforcing cues to a subject. The provision of the reinforcing cues may be triggered according to embodiments described herein.

Flowchart 1100 is described as follows. In step 1102, the second reinforcing cue is automatically provided by the stimulation device to the subject during at least a third sleep period subsequent to the second sleep period for second material of the learning category to be learned by the subject, where the first reinforcing cue is selected by the subject. That is, in embodiments a subject may be provided with the second reinforcing cue (determined in step 906) in a later sleep period for other material related to the learning category.

For example, again regarding the primary colors learning example, if the second sleep period is Thursday night in which the second reinforcing cue (e.g., sound for the word "color") is re-presented to the subject for learning primary colors in the facts learning category, on Friday or Saturday night during a subsequent sleep period the second reinforcing cue (sound for the word "color") is re-presented to the subject for learning other material in the facts learning category. Other material in the facts learning category may be, by way of example and not limitation, colors of the rainbow, colors of a flag, colors of traffic lights, colors of tropical fish, colors of stars commonly found in a given galaxy, and/or the like.

Flowchart 1200 is described as follows. In step 1202, a third reinforcing cue is automatically provided by the stimulation device to the subject during at least a third sleep period subsequent to the second sleep period for the first material of the learning category, the third reinforcing cue being similar in at least one predefined criterion to the second reinforcing cue, where the first reinforcing cue is selected by the subject. That is, in embodiments a subject may be provided with the third reinforcing cue (e.g., determined by a controller device as described herein similarly as second reinforcing cue in step 906) in a later sleep period for the material to be learned. The third reinforcing cue is similar to the second reinforcing cue in one or more aspects.

For example, again regarding the primary colors learning example, if the second reinforcing cue is the sound for the word "color," the third reinforcing cue may be automatically determined to be, and provided as, sounds of the words "red," "yellow," and/or "blue" as both the second and third reinforcing cues are related to primary colors. Taking another example, if a subject is learning facts about a forest and the second reinforcing cue is the sound of the word "forest," the third reinforcing cue may be automatically determined to be, and provided to the subject as, the sound of the word "trees," birds chirping, or the sound of pine trees blowing in the wind, as both the second and third reinforcing cues are related to forests. In some embodiments, a different type of stimulus for the third reinforcing cue maybe selected when it fulfills the requirement of being similar in at least one predefined criterion to the second reinforcing cue. For instance, an image of a forest may be projected onto the eyelids of the subject.

C. Determining Patterns of Reinforcing Cues

Patterns of reinforcing cue re-presentation during sleep of a subject may be modified to increase memory recall and reactivation efficacy. For example, patterns of reinforcing cue re-presentation during sleep may be matched with post-sleep recall accuracy, according to embodiments. Patterns resulting in high recall accuracy may be repeated during future sleep-related stimulation events while patterns resulting in poor recall accuracy are not. Patterns may be further modified as more recall accuracy data is acquired.

Patterns of reinforcing cue re-presentation during sleep may vary in frequency, intensity, volume, order, duration, timing, location, and repetition, or in additional aspects of patterns, according to embodiments. These variables may be dependent on specific brainwave patterns or eye movements within a sleep stage, a determined or predicted sleep stage, a determined or predicted sleep cycle number (e.g., first, second, third, etc.) of a sleep period, a stage or cycle progression, etc.

In embodiments, the matching of patterns to accuracy may be performed by a subject, or may be automatically performed by a device, such as controller device 102 or controller device 502 described herein.

Figure 13:
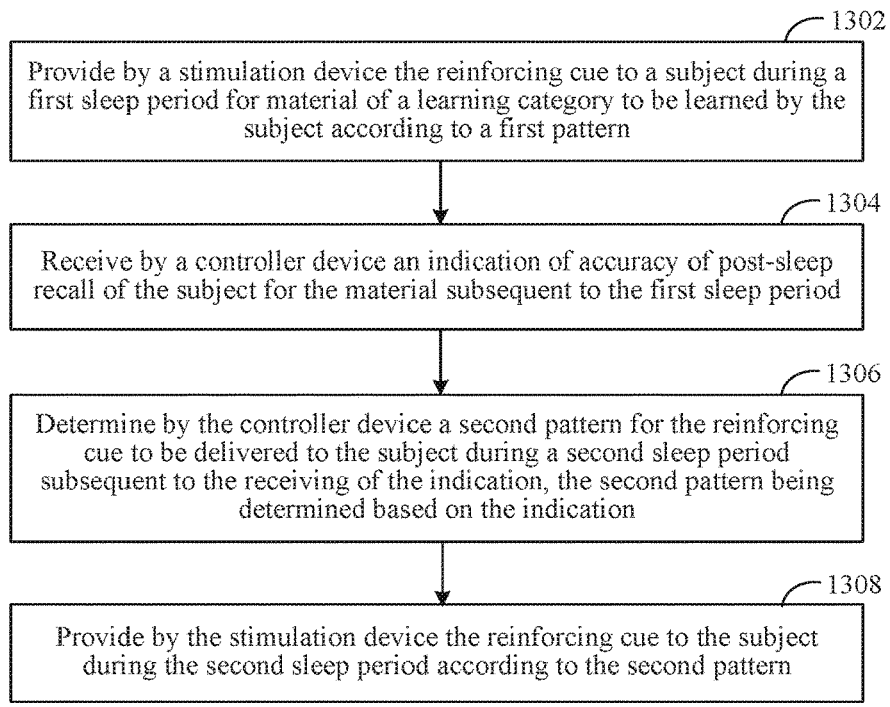
FIG. 13 is a flowchart for determining patterns for primary reinforcing cues during sleep, according to an exemplary embodiment.

FIG. 13 is a flowchart 1300 providing example steps for determining patterns for reinforcing cues during sleep, according to an exemplary embodiment. Configuration 100 of FIG. 1, system 500 of FIG. 5, and/or any of their respective components/circuits may each operate according to flowchart 1300, in embodiments. In embodiments, controller device 102 and controller device 502 are configured to execute a software program to allow a subject to identify and categorize individual items of material to be learned by the subject. Other structural and operational embodiments will be apparent to persons skilled in the relevant art(s) based on the discussion regarding flowchart 1300. Flowchart 1300 is described as follows.

Flowchart 1300 may begin with step 1302. In step 1302, a reinforcing cue is provided by a stimulation device to a subject during a first sleep period for material of a learning category to be learned by the subject according to a first pattern. In embodiments, stimulation device(s) 104 of FIGS. 1 and 3, or controller device 502 or control unit 514 of FIG. 5, may provide a reinforcing cue according to the first pattern to a subject during sleep for material of a learning category that the subject has begun to learn. For instance, a light, a sound, or a vibration may be provided in a first pattern by control unit 514 or by controller device 102 or controller device 502. Likewise, visual stimulation device 302, auditory stimulation device 304, somatosensory/vibration stimulation device 306, olfactory stimulation device 308, gustatory stimulation device 310, motion stimulation device 312, or proprioceptive stimulation device 314 of FIG. 3 may provide one or more respective stimuli. The provision of the reinforcing cue may be triggered according to embodiments described herein.

As an example, consider the learning scenario in which a subject is learning the primary colors in the context of FIG. 5. During a first period of sleep, subject 506 is provided with a reinforcing cue that comprises an auditory stimulus: sounds for the word "color." The reinforcing cue is provided by controller device 502 of FIG. 5 to subject 506 via speakers 520. The reinforcing cue may be provided according to a first pattern. The first pattern may comprise a frequency of provision (e.g., every 30 seconds, 60 seconds, 5 minutes, etc.), a duration of provision (e.g., 5 seconds of light emitted), provision during a certain portion of a sleep interval (e.g., when sleep spindles are produced in Stage II sleep), provision during a certain sleep stage or sleep cycle (e.g., during a second and third sleep cycle), or other pattern as disclosed herein.

In step 1304, an indication of accuracy of post-sleep recall of the subject for the material subsequent to the first sleep period is received by a controller device. In embodiments, controller device 102 of FIGS. 1 and 2 or controller device 502 of FIG. 5 may receive an indication of accuracy of post-sleep recall of the subject. For instance, the subject may test their post-sleep recall of the material for which the first reinforcing cue was provided in step 1302. The testing may take place during a period of wakefulness of the subject subsequent to the first period of sleep in step 1302, such as immediately or substantially immediately after waking. In embodiments, the testing may take place offline, and the subject may provide results to controller device 102 or controller device 502 through interaction with the devices. In other embodiments, controller device 102 or controller device 502 may provide the post-sleep recall test to the subject and receive answers to the test from the subject to determine an indication of accuracy. In still other embodiments, a user may be tested by, or provide an indication of accuracy to, a portion of a system backend (e.g., system backend 108 of FIG. 1) which may in turn provide the indication of accuracy to controller device 102 or controller device 502.

Continuing the learning example for primary colors, subject 506 is tested on material for the primary colors. For example, subject 506 is tested for post-sleep recall of the material during the first period of wakefulness subsequent to the first sleeping period of step 1302. Subject 506 may input answers to the test of post-sleep recall directly into controller device 102 or controller device 502, or an indication of accuracy may be provided to, and received by, controller device 102 or controller device 502 in another manner, such as those described herein. According to embodiments, the post-sleep recall test may result in a first accuracy that is at or above a threshold related to high levels of efficacy, or may result in a second accuracy that is below the threshold. In embodiments, the threshold value may be stored by controller device 102 or controller device 502 for making a determination, e.g., by comparison, of accuracy level to the threshold.

In step 1306, a second pattern for the reinforcing cue to be delivered to the subject during a second sleep period subsequent to the receiving of the indication is determined by the controller device, the second pattern being determined based on the indication. In embodiments, controller device 102 of FIGS. 1 and 2 or controller device 502 of FIG. 5 may determine a second pattern for the reinforcing cue to be delivered to the subject during a sleep period subsequent to receiving the indication of accuracy for the post-sleep recall test in step 1304. For instance, a variation over the first pattern in at least one of frequency, intensity, volume, order, duration, repetition, location, timing, and/or the like of the reinforcing cue may be determined to be provided by controller device 102 or controller device 502 (or by control unit 514 in embodiments).

In some embodiments, the second pattern of the reinforcing cue may be the same or substantially similar as the first reinforcing cue. That is, if the post-sleep recall accuracy determined in step 1304 is at or above the threshold, memory recall and reactivation with targeted stimulation is high, and the first pattern of the reinforcing cue stimulation should be maintained and re-presented in future sleep periods. On the other hand, if the post-sleep recall accuracy determined in step 1304 is below the threshold, memory recall and reactivation with targeted stimulation is low, and the first pattern of the reinforcing cue stimulation should be changed to a different pattern (e.g., a second pattern) for presentation during encoding periods and for re-presented in future sleep periods.

Continuing again with the primary colors learning example, and in the context of FIG. 5, controller device 502 may determine that post-sleep recall accuracy is below a desired level. For instance, when the subject is learning red, yellow, and blue as the primary colors, the reinforcing cue is the sound of the word "color" repeated once every 5 minutes at a given volume, and the subject expects a post-recall accuracy of better than 50% (the threshold value may be set to two correct answers), a single correct answer during post-sleep recall testing would be an indication of accuracy below the threshold, and controller device 502 determines a new, second pattern of the reinforcing cue to be used. If the accuracy exceeds the threshold (e.g., 2 or 3 correct answers), controller device 502 determines the first pattern for the reinforcing cue should continue to be used. However, in embodiments, after a specified number of encoding/learning sessions and reinforcement sleep sessions, the threshold may be raised to where accuracy for all correct answers (e.g., mastery of the material) is desired, and controller device 502 may then determine that a new pattern for reinforcing cue should be used if mastery is not yet achieved.

In embodiments, as noted above, when controller device 502 determines that a different, second pattern for the reinforcing cue should be used, it may be determined that the second pattern include a different frequency (e.g., sound for the word "color" every 30 seconds instead of every 5 minutes), a different repetition (e.g., the sound be repeated twice every 5 minutes instead of once), or that a different volume be used (e.g., volume increases, or increases each time the sound is made during a sleep stage).

The determination of what the second pattern for the reinforcing cue should be may be based on data/information from past encoding/recall testing of the subject or of other subjects (e.g., as obtained from a system backend such as system backend 108), may be based on duration of a sleep interval in which the reinforcing cue is to be re-presented, or may be determined based on input by the subject.

In some embodiments, brain waves of the subject may be monitored as a basis for determining the second pattern. For instance, if the brain waves of the subject show very high stimulation above which restful sleep may not be possible (e.g., a stimulation consistently producing a K-complex or an arousal defined as a sudden increase in EEG frequency), the intensity or volume of the first pattern may be lowered and re-represented as the second pattern.

In step 1308, the reinforcing cue is provided by the stimulation device to the subject during the second sleep period according to the second pattern. The reinforcing cue according to the second pattern may similarly be provided as described with respect to step 1302.

In some example embodiments, one or more of steps 1302, 1304, 1306, and/or 1308 of flowchart 1300 may not be performed. Moreover, steps in addition to or in lieu of steps 1302, 1304, 1306, and/or 1308 may be performed. Further, in some example embodiments, one or more of steps 1302, 1304, 1306, and/or 1308 may be performed out of order, in an alternate sequence, or partially (or completely) concurrently with other steps.

D. Predicting Sleep Interval Based on Sleep Onset

As noted above, sleep stages and sleep cycles may also be determined and/or predicted based on sleep onset time in combination with data indicating the circadian rhythmicity of the subject, using actigraphy, motion sensors, or other measurements of activity used to predict sleep and wakefulness. Sleep stages and sleep cycles may also be determined and/or predicted using sleep onset time alone.

FIG. 14 is a flowchart 1400 providing example steps for determining a sleep interval of a subject, according to an exemplary embodiment. Configuration 100 of FIG. 1, system 500 of FIG. 5, and/or any of their respective components/circuits may each operate according to flowchart 1400, in embodiments. Other structural and operational embodiments will be apparent to persons skilled in the relevant art(s) based on the discussion regarding flowchart 1400. Flowchart 1400 is described as follows.

Flowchart 1400 may begin with step 1402. In step 1402, onset of sleep of the subject is monitored by a monitoring device of the sleep system. In embodiments, as noted above, monitoring device(s) 106 of FIGS. 1 and 4 or monitoring device 504 of FIG. 5 may monitor the sleep intervals of the subject. Additionally indicia of sleep onset of subjects may be monitored. For example, aspects of the subject such as heart/pulse rate, pulse rate symmetry or variability, EEG activity, motion, lack of red reflex, or other aspects disclosed herein may be monitored by monitoring device(s) 106 of FIGS. 1 and 3 (using EEG sensor 402, EOG sensor 404, EMG sensor 406, camera 408, temperature sensor or thermo-sensor 410, vital sign sensor 412, motion sensor 414, microphone (mic) 416 of FIG. 4) or monitoring device 504 of FIG. 5 (using one or more sensors 512 of FIG. 5) for indicia of sleep onset.

In embodiments, heart/pulse rate and pulse rate symmetry or variability may be monitored by vital sign sensor 412, ocular activity may be monitored by EOG sensor 404, or neural activity may be monitored by EEG sensor 402, and information regarding the monitored aspects is proved to controller device 102 or controller device 502.

In step 1404, at least one of a sleep interval of the subject or a sleep cycle of the subject is determined by a controller device of the sleep system based on the onset of sleep, the onset of sleep being the only monitored aspect of the subject used for determining at least one of the sleep interval of the subject or the sleep cycle of the subject. In embodiments, controller device 102 of FIGS. 1 and 2 or controller device 502 of FIG. 5 may receive an indication of sleep onset of the subject via one or more monitoring devices described herein. From the indication, controller device 102 of FIGS. 1 and 2 or controller device 502 of FIG. 5 may determine that sleep onset has occurred, and based on sleep onset, the sleep interval of the subject or the sleep cycle of the subject may be determined by controller device 102 of FIGS. 1 and 2 or controller device 502 of FIG. 5 using, e.g., a timer or a schedule of subject sleep intervals.

As noted above, human adult sleep typically includes four to five sleep cycles each night where each sleep cycle is about 90 minutes in length. Additionally, sleep cycles may change in consistency as they progress through the night. For example, the percentage of slow wave sleep is high in the first sleep cycle and wanes during subsequent cycles, while the percentage of REM sleep is low in the first sleep cycle and gradually increases with subsequent cycles. Based on timing subsequent to the determined onset of sleep and/or a schedule of sleep interval lengths (e.g., that may be stored in a storage or memory of a controller device described herein), specific sleep intervals of a subject may be determined.

In step 1406, a reinforcing cue, according to one or more patterns, is provided to the subject for material of a learning category to be learned by the subject during at least one of a specific sleep stage or a specific sleep cycle based on the subject being in at least one of the specific sleep stage or the specific sleep cycle. In embodiments, stimulation device(s) 104 of FIGS. 1 and 3 or controller device 502 of FIG. 5 may provide the reinforcing cue according to one or more patterns to the subject during a sleep interval determined based on the onset of sleep. Provision of the reinforcing cue and the pattern(s) used may be in accordance with the embodiments described herein.

In some example embodiments, one or more of steps 1402, 1404, and/or 1406 of flowchart 1400 may not be performed. Moreover, steps in addition to or in lieu of steps 1402, 1404, and/or 1406 may be performed. Further, in some example embodiments, one or more of steps 1402, 1404, and/or 1406 may be performed out of order, in an alternate sequence, or partially (or completely) concurrently with other steps.

In additional embodiments, sleep stages and sleep cycles may also be determined and/or predicted based on sleep onset time, as described in flowchart 1400, in combination with data indicating the circadian rhythmicity of the subject, using actigraphy, motion sensors, or other measurements of activity used to predict sleep and wakefulness.

Furthermore, controller device 102 of FIGS. 1 and 2 and/or controller device 502 of FIG. 5 are configured to determine the sleep interval of a subject upon sleep onset after a relatively short period of wakefulness during typical sleep time periods. For example, controller device 102 of FIGS. 1 and 2 and/or controller device 502 of FIG. 5 may track the current sleep interval of a subject and maintain what the sleep stage and/or sleep cycle of the subject would have been had the subject not woken up. This type of sleep interval prediction may be similarly used to determine when reinforcing cues are re-presented to the subject.

E. Additional Operational Embodiments

Any of the preceding embodiments may be further modified according to the example operational embodiments in this subsection. For instance, one or more of flowcharts 700, 800, 900, 1000, 1100, 1200, 1300, and/or 1400 may include some or all portions of the embodiments described below. Configuration 100 of FIG. 1, system 500 of FIG. 5, and/or any of their respective components/circuits may each operate according to embodiments in this subsection.

Turning now to FIG. 15, a flowchart 1500 for memory encoding is depicted, according to example embodiments. Flowchart 1500 includes step 1502. In step 1502, the reinforcing cue is provided to the subject during wakefulness of the subject preceding the subject being asleep and while the subject was learning material of the learning category. In embodiments, step 1502 may be performed prior to step 808 in flowchart 800 of FIG. 8, prior to step 902 in flowchart 900 of FIG. 9, and/or prior to step 1302 in flowchart 1300 of FIG. 13. In embodiments, stimulation device(s) 104 of FIGS. 1 and 3 or controller device 502 of FIG. 5 may provide a reinforcing cue to the subject, during wakefulness prior to sleep, for material of a learning category that the subject has begun to learn. Likewise, visual stimulation device 302, auditory stimulation device 304, somatosensory/vibration stimulation device 306, olfactory stimulation device 308, gustatory stimulation device 310, motion stimulation device 312, or proprioceptive stimulation device 314 of FIG. 3 may provide one or more respective stimuli for memory encoding. For instance, a light, a sound, or a vibration (or other stimuli described or contemplated herein) may be provided to the subject for memory encoding during wakefulness.

FIG. 16 is a diagram of a configuration 1600 for stimulation provision for memory encoding, according to an example embodiment. Configuration 1600 includes one or more sensors for providing stimulation, such as a primary or secondary reinforcing cue, to subject 506. As shown, a first stimulation device 1602, a second stimulation device 1604, a third stimulation device 1606, a fourth stimulation device 1608, and a fifth stimulation device 1610 are affixed to the fingers of subject 506. Each stimulation device may be connected to a controller device (e.g., controller device 102 or controller device 502) by connectors 1612 that may be wired or wireless in embodiments. The controller device may be configured to control the provision of stimulation from the stimulation devices. While five stimulation devices are shown in configuration 1600, it is contemplated and more or fewer may be included in embodiments. Additionally, it is contemplated herein that different locations (i.e., any locations) on, or in the environment of, the body of subject 506 may be used for the stimulation devices, and that different patterns may be used for different locations for a single application of a stimulus.

First stimulation device 1602, second stimulation device 1604, third stimulation device 1606, fourth stimulation device 1608, and fifth stimulation device 1610 may be configured to be attached to subject 506 by clips, patches/adhesives, bands, and/or the like. In the illustrated embodiment, first stimulation device 1602, second stimulation device 1604, third stimulation device 1606, fourth stimulation device 1608, and fifth stimulation device 1610 are configured to provide vibrational or somatosensory stimuli to the fingers of subject 506. In other embodiments, these stimulation devices may provide temperature stimuli, auditory stimuli, visual stimuli, motion or movement stimuli, and/or the like.

Furthermore, first stimulation device 1602, second stimulation device 1604, third stimulation device 1606, fourth stimulation device 1608, and fifth stimulation device 1610 may be configured to provide respective stimuli in patterns. For instance, each stimulation device may provide its stimulus at approximately the same time or sequentially. Sequential stimulation between stimulation devices may be partially overlapping in application/duration. Still further, the stimulation devices may be programmed to provide different stimulation patterns in different locations, such as a specific pattern of stimulation that matches the playing of a musical instrument (e.g., a piano or guitar) the subject is learning to play. In such an embodiment, the fingers of subject 506 may be stimulated by vibration or movement according to a song or sound that is learned during memory encoding in a wakeful state. In an embodiment, a controller device such as controller devices 102 and/or 502 may play the music to be learned, with or without video accompaniment, and simultaneously provide stimulation via first stimulation device 1602, second stimulation device 1604, third stimulation device 1606, fourth stimulation device 1608, and fifth stimulation device 1610 to subject 506. A similar configuration may be applied to both hands of subject 506 in embodiments.

As described herein, the stimulation provided to a subject, e.g., as with respect to flowchart 1500 and configuration 1600, may also be repeated and re-presented to the subject during sleep as targeted stimulation for memory recall and reactivation. Other structural and operational embodiments will be apparent to persons skilled in the relevant art(s) based on the discussion herein.

As noted above, stimuli may be provided according to patterns. FIG. 17 is a flowchart 1700 for providing reinforcing cues according to one or more patterns, according to example embodiments. Flowchart 1700 includes step 1702. In step 1702, the reinforcing cue is provided in one or more patterns that comprise a variation in at least one of frequency, intensity, volume, order, duration, repetition, timing, location, or content. That is, each of these variables may be changed or altered within a given stimulation, from stimulation to stimulation, within a sleep stage, from sleep stage to sleep stage, based on a sleep cycle or a progression thereof, based on subject information (e.g., age, sex, motor skill level, disabilities, predispositions, education level, sensitivity to stimuli, etc.), information related to past memory encoding and post-sleep recall, subject preference, and/or the like.

Additionally, a default cue or a pattern for a given stimulation type may be initially provided to a subject according to embodiments. For example, a default volume for a specific auditory cue, a default brightness for visual cues, a specific visual cue, a default vibrational amplitude, etc., may be used. In some embodiments, defaults may be determined according to system backend 108 of FIG. 1 based on collected and stored information. The determination of default pattern for the reinforcing cue should be may be based on data/information from past encoding/recall testing of the subject or of other subjects (e.g., as obtained from a system backend such as system backend 108), may be based on duration of a sleep interval in which the reinforcing cue is to be re-presented, or may be determined based on input by the subject.

In addition to defaults, controller device 102 and/or controller device 502 may suggest changes in reinforcing cues and/or patterns based analysis by system back 108.

In embodiments, step 1702 may be performed as part of step 808 in flowchart 800 of FIG. 8, as part of steps 902 and/or 906 in flowchart 900 of FIG. 9, and/or as part of steps 1302 and/or 1308 in flowchart 1300 of FIG. 13.

FIG. 18 is a flowchart 1800 for testing post-sleep recall accuracy, according to example embodiments. Flowchart 1800 includes step 1802. In step 1802, the post-sleep recall of the subject is tested for the material to determine the indication of accuracy. In embodiments, subjects may test their post-sleep recall of the material to be learned and for which reinforcing cues are provided. The testing may take place during a period of wakefulness of the subject subsequent to a period of sleep with reinforcing cues presented. The period of wakefulness may be immediately or substantially immediately after waking, or a predetermined time after waking. In embodiments, the testing may take place offline, and the subject may provide results to controller device 102 or controller device 502 through interaction with the devices. In other embodiments, controller device 102 or controller device 502 may provide the post-sleep recall test to the subject and receive answers to the test from the subject to determine an indication of accuracy. It is contemplated herein that accuracy of post-sleep recall testing may be tracked according to a percentage of correct answers and/or according to types of answers correct or incorrect, e.g., by a controller device or system backend 108, and trends for improvement or regression may be determined. In still other embodiments, a user may be tested by, or provide an indication of accuracy to, a portion of a system backend (e.g., system backend 108 of FIG. 1) which may in turn provide the indication of accuracy to controller device 102 or controller device 502. In the motor skill category, a user may provide a template for motion (e.g., an electronic representation), a testing apparatus (e.g., electronic keyboard), or the like and test accuracy against the template. In some embodiments, a subject may self-report results or a proctor or teacher may report results.

According to embodiments, primary reinforcing cues and/or secondary reinforcing cues may be tested in post-sleep recall accuracy testing for any number of materials and learning categories, and across multiple types of stimuli.

It is also contemplated herein that cues may be provided to a subject during testing of post-sleep recall. That is, a subject may be provided with a stimulus while learning while at the same time being tested by a device, mechanism, or party. In other words, pre-sleep encoding with stimuli and post-sleep recall testing may occur at the same time.

In embodiments, step 1802 may be performed prior to step 904 in flowchart 900 of FIG. 9, and/or prior to step 1304 in flowchart 1300 of FIG. 13.

V. Further Example Embodiments and Advantages

As previously noted, systems and devices may be configured in various ways according to the embodiments and techniques described herein. For example, while system 500 of FIG. 5 includes controller device 502 and monitoring device 504 that is wearable on a wrist of subject 506, many other monitoring and stimulation devices/apparatuses are described herein. For example, FIG. 19 is a sensor configuration 1900, according to an embodiment. Sensor configuration 1900 includes a sensor device 1902 that may be communicatively coupled to a controller device (e.g., controller device 102 and/or controller device 502) via a connection 1904 that may be wired or wireless. While one sensor device 1902 is illustrated, more may be included in embodiments.

In the illustrated embodiment, sensor device 1902 is configured to monitor one or more aspects of subject 506 such as vital signs 1906, which may be by way of example and not limitation, pulse/heart rate, pulse rate variations or symmetry, blood pressure, blood oxygen saturation, skin resistivity, body temperature, etc. Sensor device 1902 is also configured to provide information related to the monitored aspects of subject 506 (i.e., vital signs 1906) to a controller device via connection 1904 as described herein where such information may be used to determine sleep intervals, patterns of reinforcing cues and stimuli, when reinforcing cues and stimuli are delivered, etc.

Sensor device 1902 may be a further embodiment of temperature sensor or thermo-sensor 410 or vital sign sensor 412 of FIG. 4. In some embodiments, sensor device 1902 may also comprise one or more stimulation devices as described herein.

FIG. 20 is a sensor configuration 2000, according to an embodiment. Sensor configuration 2000 includes a first sensor device 2002 and a second sensor device 2004 that may be communicatively coupled to a controller device (e.g., controller device 102 and/or controller device 502) via connections 2006 that may be wired or wireless. While two sensor devices 2002 and 2004 are shown, more or fewer may be included according to embodiments herein.

In the illustrated embodiment, first sensor device 2002 and second sensor device 2004 are configured to monitor one or more aspects of subject 506 such as EEG. First sensor device 2002 and second sensor device 2004 also configured to provide information related to the monitored aspects of subject 506 (e.g., EEG) to a controller device as described herein where such information may be used to determine sleep intervals, patterns of reinforcing cues and stimuli, when reinforcing cues and stimuli are delivered, etc.

First sensor device 2002 and second sensor device 2004 may be a further embodiment of EEG sensor 402 of FIG. 4. In some embodiments, first sensor device 2002 and/or second sensor device 2004 may also comprise one or more stimulation devices as described herein.

Figure 21:
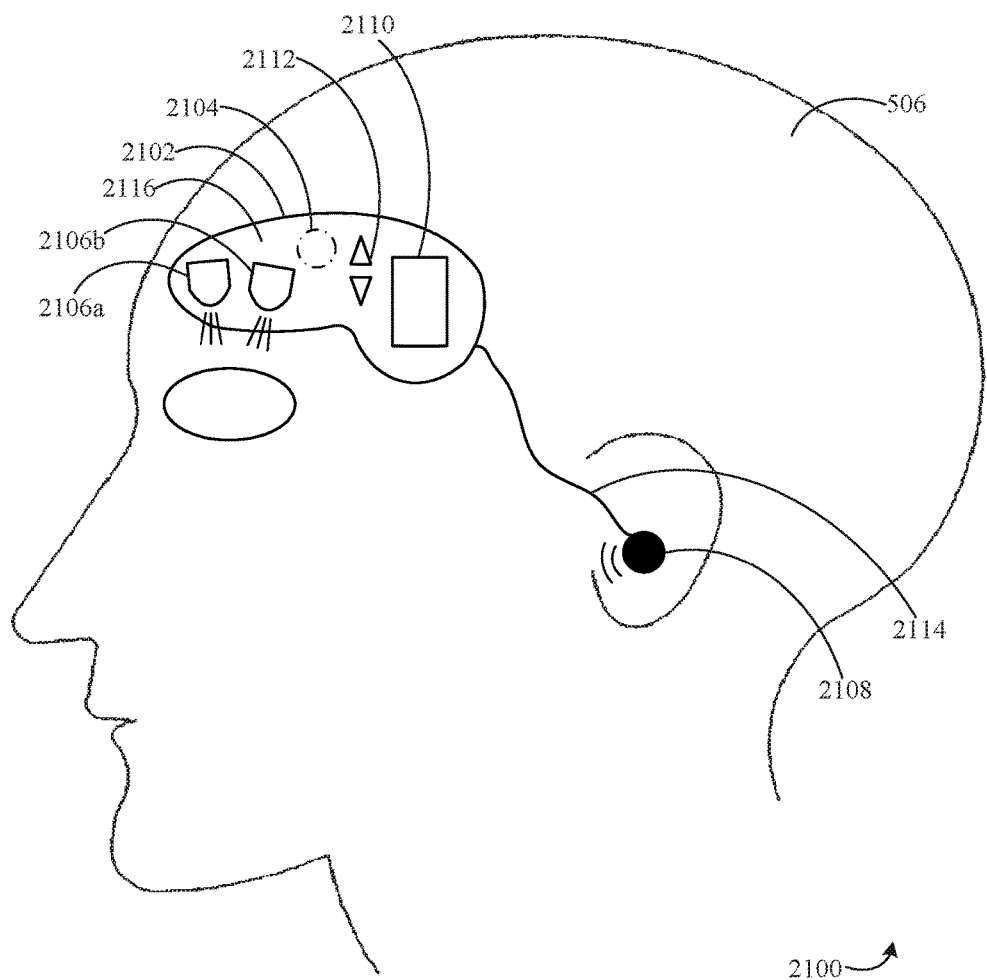
FIG. 21 is a diagram of a wearable device configuration, according to an exemplary embodiment.

Another type of wearable device, according to embodiments, is depicted in FIG. 21. FIG. 21 is a diagram of a wearable device configuration 2100. Wearable device configuration 2100 includes a wearable device 2102 that is configured to be worn by, or affixed to, subject 506. Wearable device 2102 of wearable device configuration 2100 is configured to monitor aspects of subject 506 and to provide stimuli (reinforcement cues) to subject 506. Wearable device 2102 includes a band 2116 (or strip or patch), one or more sensors 2104, and a control unit 2110.

Wearable device 2102 includes visual stimulation devices 2106a-2106b. As depicted, the visual stimulation devices 2106a-2106b may be one or more light-emitting devices (such as, e.g., a pair or more of light-emitting diodes). The visual stimulation devices 2106a-2106b may emit visually perceived patterns such as one or more colors of light of varying brightness, frequency, intensity, etc. In embodiments, 2106a-2106b visual stimulation devices may be oriented to provide directionality of individual light sources. Wearable device 2102 also includes a speaker 2108 configured to deliver auditory reinforcement cues and stimulation from the band 2116 to subject 506 via a connection 2114 that may be wired or wireless.

One or more sensors 2104 may be affixed to, or a part of, wearable device 2102 and may be one or more of the sensors described herein. In embodiments, one or more of the sensors 2104 may reside on the inside of band 2116 closer to, or next to, the skin of subject 506. Control unit 2110 may be affixed to or part of wearable device 2102 and may include a processing device or processing circuitry, a memory, communication circuitry, a user interface (UI), a display, a vibration component, and/or the like. In embodiments, control unit 2110 is configured to operate and function as a controller device, such as those described herein. In other embodiments, control unit 2110 is configured to provide information monitored by one or more sensors 2104, and that relates to one or more aspects of subject 506, to a controller device such as controller device 102 and/or controller device 502.

A subject such as subject 506 may interact with a UI 2112 to activate a variety of features for wearable device 2102. For example, subject 506 may enable or disable various components of Wearable device 2102 (e.g., auditory stimulation apparatus, visual stimulation apparatus, monitoring apparatus, etc.), alter various parameters of the monitoring apparatus (e.g., sensitivity, sampling rate, filters, etc.), change the stimulation being delivered, alter patterns or parameters of the stimulation (e.g., volume, frequency, brightness, color, duration, repetition, stimulation sleep interval, etc.), etc. In embodiments, wearable device 2102 may include fewer or additional features for UI 2112. Further, although this embodiment depicts buttons, UI 2112 may include switches, toggles, touch screens, etc.

The embodiments described in this subsection may be adapted to any wearable electronic devices and/or sensors, as well as communication devices and computing devices, described herein.

In embodiments, while learning complex associations among a group of facts, a subject may draw out or otherwise obtain a visual representation of the associations, such as but not limited to, a flow chart, a Venn diagram, a hierarchical list, a table, or other visual depiction of the interconnections of multiple facts or relationships to be learned. Such visual representation may then be used during learning while awake and then again during sleep as visual reinforcing cues.

Furthermore, according to embodiments, a subject may learn more than one set of material in one or more learning categories at one time. In such cases, different types of stimulations (e.g., primary and/or secondary reinforcing cues for auditory, somatosensory, visual, etc.) may be provided to the subject during sleep. In embodiments, the different types of stimulations may be in different patterns than each other as well as in different locations, and may or may not overlap with each other.

One or more embodiments described herein may perform their functions according to the flowcharts described herein. Additional structural and operational embodiments will be apparent to persons skilled in the relevant art(s) based on the discussions regarding the flowcharts and embodiments herein. In some example embodiments, one or more of the steps of the described flowcharts may not be performed. Moreover, steps in addition to or in lieu of the steps of the described flowcharts may be performed (some of which were described above). Further, in some example embodiments, one or more of the steps of the described flowcharts may be performed out of the order shown or described, in an alternate sequence, and/or partially (or completely) concurrently with other steps.

The memory recall and reactivation by targeted stimulation embodiments and/or any further systems, sub-systems, and/or components disclosed herein may be implemented in hardware (e.g., hardware logic/electrical circuitry), or any combination of hardware with software (computer program code configured to be executed in one or more processors or processing devices) and/or firmware. In embodiments, sensors and stimulation devices may be part of the device or apparatus.

One or more embodiments described herein may be used in a clinical setting or in a private setting such as the subject's home. In embodiments, such as the clinic setting, it is contemplated that sleep interval may be tracked manually and indicia thereof may be provided to a controller device as described herein.

VI. Example Electronic and Computing Device Embodiments

Figure 22:
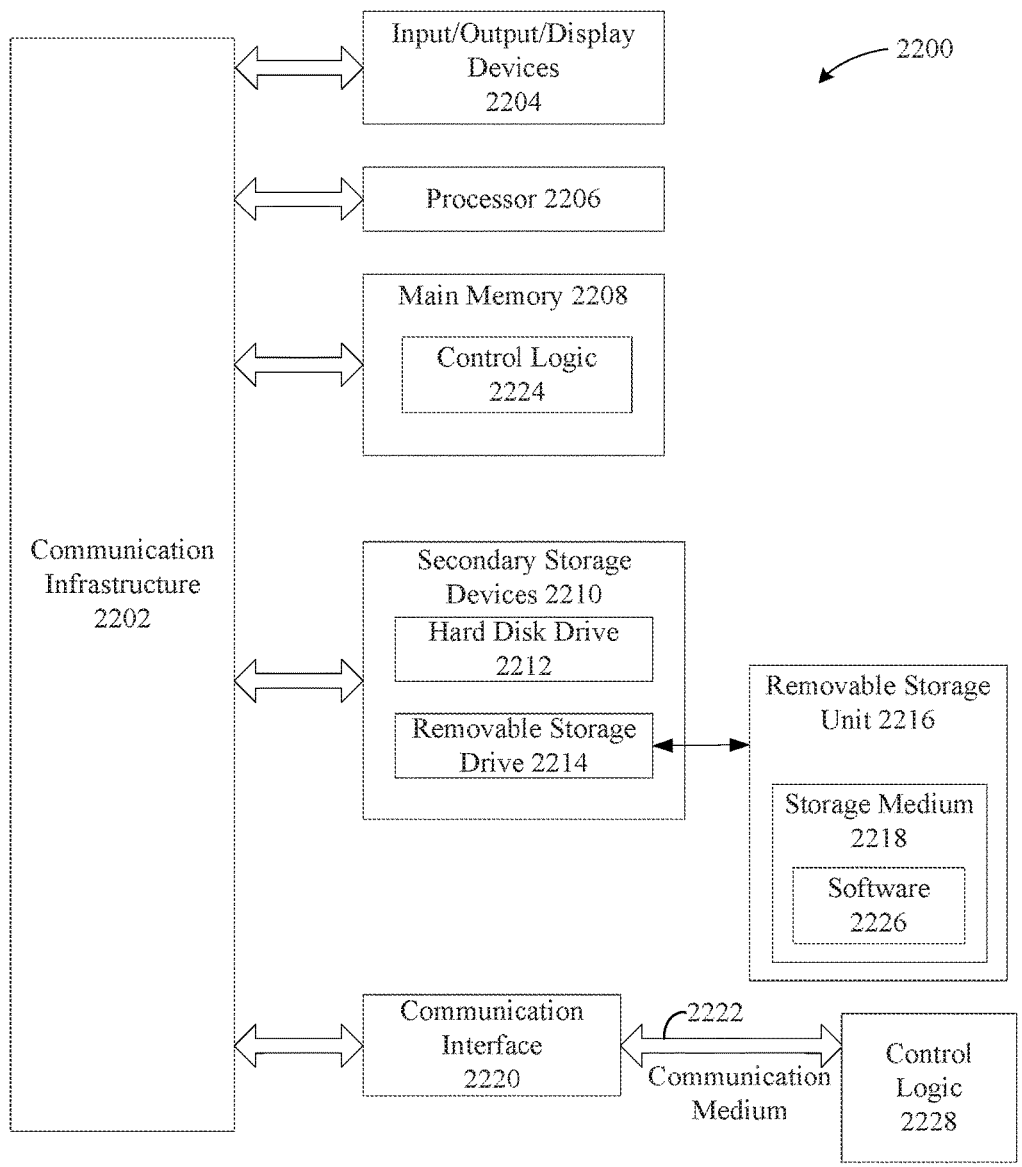
FIG. 22 is a block diagram of a computer system, according to an exemplary embodiment.

The embodiments described herein, including systems, methods/processes, devices, and/or apparatuses, may be implemented at least in part using known processing devices, telephones (smart phones and/or mobile phones), wearable fitness trackers, smart watches, other wearable computing and electronic devices, tablet computers, servers, and/or, computers, such as a computer 2200 shown in FIG. 22. It should be noted that computer 2200 may represent communication devices, processing and electronic devices, servers, and/or traditional computers in one or more embodiments. For example, the memory recall and reactivation by targeted stimulation embodiments, and any of the subsystems or components respectively contained therein, may be implemented at least in part using one or more computers 2200 or portions thereof.

Computer 2200 can be any commercially available and known communication device, processing device, electronic device, and/or computer capable of performing the functions described herein, such as devices/computers available from International Business Machines®, Apple®, Sun®, HP®, Dell®, Cray®, Samsung®, Nokia®, etc. Computer 2200 may be any type of computer, including a desktop computer, a server, etc.

Computer 2200 includes one or more processors (also called central processing units, or CPUs), such as a processor 2206. Processor 2206 is connected to a communication infrastructure 2202, such as a communication bus. In some embodiments, processor 2206 can simultaneously operate multiple computing threads.

Computer 2200 also includes a primary or main memory 2208, such as random access memory (RAM). Main memory 2208 has stored therein control logic 2224 (computer software), and data.

Computer 2200 also includes one or more secondary storage devices 2210. Secondary storage devices 2210 include, for example, a hard disk drive 2212 and/or a removable storage device or drive 2214, as well as other types of storage devices, such as memory cards and memory sticks. For instance, computer 2200 may include an industry standard interface, such as a universal serial bus (USB) interface for interfacing with devices such as a memory stick. Removable storage drive 2214 represents a floppy disk drive, a magnetic tape drive, a compact disk drive, an optical storage device, tape backup, etc.

Removable storage drive 2214 interacts with a removable storage unit 2216. Removable storage unit 2216 includes a computer useable or readable storage medium 2218 having stored therein computer software 2226 (control logic) and/or data. Removable storage unit 2216 represents a floppy disk, magnetic tape, compact disk, DVD, optical storage disk, or any other computer data storage device. Removable storage drive 2214 reads from and/or writes to removable storage unit 2216 in a well-known manner.

Computer 2200 also includes input/output/display devices 2204, such as touchscreens, LED and LCD displays, monitors, keyboards, pointing devices, etc.

Computer 2200 further includes a communication or network interface 2218. Communication interface 2220 enables computer 2200 to communicate with remote devices. For example, communication interface 2220 allows computer 2200 to communicate over communication networks or mediums 2222 (representing a form of a computer useable or readable medium), such as LANs, WANs, the Internet, etc. Network interface 2220 may interface with remote sites or networks via wired or wireless connections.

Control logic 2228 may be transmitted to and from computer 2200 via the communication medium 2222.

Any apparatus or manufacture comprising a computer useable or readable medium having control logic (software) stored therein is referred to herein as a computer program product or program storage device. This includes, but is not limited to, computer 2200, main memory 2208, secondary storage devices 2210, and removable storage unit 2216. Such computer program products, having control logic stored therein that, when executed by one or more data processing devices, cause such data processing devices to operate as described herein, represent embodiments of the invention.

Techniques, including methods, and embodiments described herein may be implemented by hardware (digital and/or analog) or a combination of hardware with one or both of software and/or firmware. Techniques described herein may be implemented by one or more components. Embodiments may comprise computer program products comprising logic (e.g., in the form of program code or software as well as firmware) stored on any computer useable medium, which may be integrated in or separate from other components. Such program code, when executed by one or more processor circuits, causes a device to operate as described herein. Devices in which embodiments may be implemented may include storage, such as storage drives, memory devices, and further types of physical hardware computer-readable storage media. Examples of such computer-readable storage media include, a hard disk, a removable magnetic disk, a removable optical disk, flash memory cards, digital video disks, random access memories (RAMs), read only memories (ROM), and other types of physical hardware storage media. In greater detail, examples of such computer-readable storage media include, but are not limited to, a hard disk associated with a hard disk drive, a removable magnetic disk, a removable optical disk (e.g., CDROMs, DVDs, etc.), zip disks, tapes, magnetic storage devices, MEMS (micro-electromechanical systems) storage, nanotechnology-based storage devices, flash memory cards, digital video discs, RAM devices, ROM devices, and further types of physical hardware storage media. Such computer-readable storage media may, for example, store computer program logic, e.g., program modules, comprising computer executable instructions that, when executed by one or more processor circuits, provide and/or maintain one or more aspects of functionality described herein with reference to the figures, as well as any and all components, capabilities, and functions therein and/or further embodiments described herein.

Such computer-readable storage media are distinguished from and non-overlapping with communication media (do not include communication media). Communication media embodies computer-readable instructions, data structures, program modules or other data in a modulated data signal such as a carrier wave. The term "modulated data signal" means a signal that has one or more of its characteristics set or changed in such a manner as to encode information in the signal. By way of example, and not limitation, communication media includes wireless media such as acoustic, RF, infrared and other wireless media, as well as wired media and signals transmitted over wired media. Embodiments are also directed to such communication media.

The techniques and embodiments described herein may be implemented as, or in, various types of devices and apparatuses. For instance, embodiments may be included, without limitation, in processing devices (e.g., illustrated in FIG. 22) such as computers and servers, as well as communication devices such as smart phones, smart watches, wearable electronic devices, home electronics, gaming consoles, entertainment devices/systems, etc. A device, as defined herein, is a machine or manufacture as defined by 35 U.S.C. § 101. That is, as used herein, the term "device" refers to a machine or other tangible, manufactured object or apparatus, and excludes software and signals. Devices may include digital circuits, analog circuits, or a combination thereof. Devices may include one or more processor circuits (e.g., central processing units (CPUs), processor 2206 of FIG. 22), microprocessors, digital signal processors (DSPs), and further types of physical hardware processor circuits) and/or may be implemented with any semiconductor technology in a semiconductor material, including one or more of a Bipolar Junction Transistor (BJT), a heterojunction bipolar transistor (HBT), a metal oxide field effect transistor (MOSFET) device, a metal semiconductor field effect transistor (MESFET) or other transconductor or transistor technology device. Such devices may use the same or alternative configurations other than the configuration illustrated in embodiments herein.

VII. Conclusion

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

What is claimed is:

1. A method for providing patterns of a reinforcing cue re-presentation during sleep, comprising:
   receiving an indication of a learning category that a subject has begun to learn by a control apparatus;
   monitoring sleep intervals of the subject while the subject is asleep by a monitoring apparatus;
   determining that the subject is in a specific sleep interval by the control apparatus;
   providing by a stimulation apparatus the reinforcing cue for the learning category to the subject according to one or more patterns during the specific sleep interval based on the subject being in the specific sleep interval;
   receiving by the control apparatus an indication of accuracy of post-sleep recall of the subject for material of the learning category subsequent to the specific sleep interval; and
   determining by the control apparatus a different pattern for the reinforcing cue to be delivered to the subject during a subsequent sleep interval after the receiving of the indication, the different pattern being determined based on the indication.

2. The method of claim 1, wherein the one or more patterns comprise at least two patterns that overlap in one or more of application, location, and duration; or
   further comprising:
   providing by the stimulation apparatus another reinforcing cue for the learning category to the subject according to one or more additional patterns during the specific sleep interval based on the subject being in the specific sleep interval, wherein the one or more patterns and the one or more additional patterns overlap in one or more of application, location, and duration.

3. The method of claim 1, wherein the one or more patterns comprise a variation in at least one of frequency, intensity, volume, order, duration, repetition, or timing of the reinforcing cue.

4. The method of claim 3, wherein the reinforcing cue was previously provided to the subject during wakefulness of the subject preceding the subject being asleep and while the subject was learning the material of the learning category.

5. The method of claim 4, further comprising at least one of:
   the learning category being motor skills, and the specific sleep interval being one or more of slow wave sleep and stage II sleep;
   the learning category being creative thought, and the specific sleep interval being rapid eye movement (REM) sleep; or
   the learning category being facts, and the specific sleep interval being slow wave sleep.

6. The method of claim 1, wherein the specific sleep interval comprises one or more of stage I sleep, stage II sleep, slow wave sleep, and rapid eye movement (REM) sleep, a sleep cycle, a progression of sleep stages within a sleep cycle, or a progression of sleep cycles throughout a sleep period.

7. The method of claim 1, wherein monitoring the sleep interval is performed by the monitoring apparatus according to one or more of electroencephalography (EEG), electromyography (EMG), electro-oculography (EOG), motion sensing, eye movement, breathing, skin temperature, pulse rate, pulse rate symmetry, or pulse rate variability of the subject.

8. The method of claim 1, wherein the control apparatus is a smartphone or a wearable electronic device.

9. The method of claim 1, further comprising at least one of:
   providing by the stimulation apparatus the reinforcing cue to the subject during the subsequent sleep interval according to the second pattern; or
   testing the post-sleep recall of the subject for the material to determine the indication of accuracy.

10. The method of claim 9, further comprising:
    automatically providing by the stimulation apparatus the reinforcing cue according to the second pattern to the subject during at least a further subsequent sleep interval.

11. The method of claim 4, further comprising:
    determining by the control apparatus another reinforcing cue to be delivered to the subject during a later specific sleep interval subsequent to the receiving of the indication, the other reinforcing cue being based on the indication.

12. The method of claim 11, wherein the reinforcing cue is at least one of a first visual stimulation, a first somatosensory stimulation, or a first auditory stimulation; and wherein the other reinforcing cue is one or more of:
- at least one of a second visual stimulation, a second somatosensory stimulation, or a second auditory stimulation that is different from the reinforcing cue, the other reinforcing cue determined by the control apparatus to be different from the first reinforcing cue based on the indication indicating an accuracy below a threshold accuracy level; or
- at least one of a second visual stimulation, a second somatosensory stimulation, or a second auditory stimulation that is approximately the same as the reinforcing cue, the other reinforcing cue determined by the control apparatus to be approximately the same as the first reinforcing cue based on the indication indicating an accuracy above the threshold accuracy level.

13. The method of claim 12, further comprising:
providing by the stimulation apparatus the other reinforcing cue to the subject during the later specific sleep interval and during at least an additional specific sleep interval subsequent to the later specific sleep interval.

14. The method of claim 13, wherein the reinforcing cue is selected by the subject, the method further comprising at least one of:
- automatically providing by the stimulation apparatus the other reinforcing cue to the subject during at least a first sleep interval subsequent to the later specific sleep interval for additional material of the learning category to be learned by the subject, or
- automatically providing by the stimulation apparatus an additional reinforcing cue to the subject during at least a first sleep interval subsequent to the later specific sleep interval for the material of the learning category, the additional reinforcing cue being similar in at least one predefined criterion to the other reinforcing cue; or wherein the reinforcing cue is a primary reinforcing cue, the method further comprising:
- providing by the stimulation apparatus a first secondary reinforcing cue to the subject during learning wakefulness and then during the specific sleep interval for the material, and
- determining by the controller apparatus a second secondary reinforcing cue to be delivered to the subject during a future sleep interval subsequent to the receiving of the indication, the second secondary reinforcing cue being based on the indication.

15. A system for providing patterns of a reinforcing cue re-presentation during sleep, comprising:
- a monitoring apparatus configured to monitor sleep intervals of a subject while the subject is asleep;
- a control apparatus configured to:
  - receive an indication of a learning category that a subject has begun to learn; and
  - determine that the subject is in a specific sleep interval; and
- a stimulation apparatus configured to provide the reinforcing cue for the learning category to the subject according to one or more patterns during the specific sleep interval based on the subject being in the specific sleep interval;
- the control apparatus further configured to:
  - receive an indication of accuracy of post-sleep recall of the subject for material of the learning category subsequent to the specific sleep interval; and
  - determine a different pattern for the reinforcing cue to be delivered to the subject during a subsequent sleep interval after the receiving of the indication, the different pattern being determined based on the indication.

16. The system of claim 15, including at least one of:
- wherein the one or more patterns comprise at least two patterns that overlap in one or more of application, location, and duration;
- wherein the stimulation apparatus is configured to provide another reinforcing cue for the learning category to the subject according to one or more additional patterns during the specific sleep interval based on the subject being in the specific sleep interval, wherein the one or more patterns and the one or more additional patterns overlap in one or more of application, location, and duration; or
- wherein the one or more patterns comprise a variation in at least one of frequency, intensity, volume, order, duration, repetition, or timing of the reinforcing cue.

17. The system of claim 16, wherein the reinforcing cue was previously provided to the subject during wakefulness of the subject preceding the subject being asleep and while the subject was learning the material of the learning category.

18. The system of claim 17, wherein the learning category is motor skills, and the specific sleep interval is one or more of slow wave sleep or stage II sleep;
- wherein the learning category is creative thought, and the specific sleep interval is rapid eye movement (REM) sleep; or
- wherein the learning category is facts, and the specific sleep interval is slow wave sleep.

19. The system of claim 15, wherein the specific sleep interval comprises one or more of stage I sleep, stage II sleep, slow wave sleep, and rapid eye movement (REM) sleep, a sleep cycle, a progression of sleep stages within a sleep cycle, or a progression of sleep cycles throughout a sleep period; or
- wherein monitoring the sleep interval is performed by the monitoring apparatus according to one or more of electroencephalography (EEG), electromyography (EMG), electro-oculography (EOG), motion sensing, eye movement, breathing, skin temperature, pulse rate, pulse rate symmetry, or pulse rate variability of the subject.

20. The system of claim 15, wherein the control apparatus is a smartphone or a wearable electronic device.

21. A computer-readable storage medium having program instructions recorded thereon that, when executed by a processing device, perform a method for providing patterns of a reinforcing cue re-presentation during sleep, the method comprising:
- receiving an indication of a learning category that a subject has begun to learn by a control apparatus;
- monitoring sleep intervals of the subject while the subject is asleep by a monitoring apparatus;
- determining that the subject is in a specific sleep interval by the control apparatus;
- providing by a stimulation apparatus the reinforcing cue for the learning category to the subject according to one or more patterns during the specific sleep interval based on the subject being in the specific sleep interval, the one or more patterns comprising a variation in at least one of frequency, intensity, volume, order, duration, repetition, or timing of the reinforcing cue, and the reinforcing cue having been previously provided to the subject during wakefulness of the subject preceding the subject being asleep and while the subject was learning material of the learning category;

receiving by the control apparatus an indication of accuracy of post-sleep recall of the subject for the material subsequent to the specific sleep interval; and determining by the control apparatus another reinforcing cue to be delivered to the subject during a later specific sleep interval subsequent to the receiving of the indication, the other reinforcing cue being based on the indication.

22. The computer-readable storage medium of claim 21, wherein the method further comprises:

determining by the control apparatus a different pattern for the reinforcing cue to be delivered to the subject during a subsequent sleep interval after the receiving of the indication, the different pattern being determined based on the indication.

\* \* \* \* \*